(12) United States Patent
Wang et al.

(10) Patent No.: US 6,727,096 B1
(45) Date of Patent: Apr. 27, 2004

(54) ANALYSIS AND CONTROL OF PARALLEL CHEMICAL REACTIONS

(75) Inventors: Pei Wang, San Jose, CA (US); G. Cameron Dales, Palo Alto, CA (US)

(73) Assignee: Symyx Technologies, Inc., Santa Clara, CA (US)

(*) Notice: Subject to any disclaimer, the term of this patent is extended or adjusted under 35 U.S.C. 154(b) by 69 days.

(21) Appl. No.: 09/723,720

(22) Filed: Nov. 28, 2000

Related U.S. Application Data

(60) Division of application No. 09/239,223, filed on Jan. 29, 1999, now Pat. No. 6,489,168, which is a continuation-in-part of application No. 09/211,982, filed on Dec. 14, 1998, now Pat. No. 6,306,658, which is a continuation-in-part of application No. 09/177,170, filed on Oct. 22, 1998, now Pat. No. 6,548,026.
(60) Provisional application No. 60/096,603, filed on Aug. 13, 1998.

(51) Int. Cl.[7] .......................... G01N 31/10; B01J 19/00
(52) U.S. Cl. .......................... 436/37; 422/62; 422/130; 422/196; 422/197; 436/34; 436/43; 436/50; 436/55; 436/85; 436/147; 436/159; 700/266; 700/268; 700/269
(58) Field of Search .......................... 422/62, 102, 104, 422/93, 196–197, 105, 107, 108, 112, 130; 436/34, 37, 43, 50, 55, 85, 147, 159, 161, 164, 173; 700/266, 268, 269

(56) References Cited

U.S. PATENT DOCUMENTS 2,991,161 A    7/1961   Gasche (List continued on next page.)

FOREIGN PATENT DOCUMENTS

| CS | 266759 | 6/1990 |
| EP | 0 529 504 A2 | 3/1993 |

(List continued on next page.)

OTHER PUBLICATIONS

Hazard Evaluation Laboratory Inc., *Affordable Reaction Calorimetry: Efficient Process Development and Hazard Assessment*, undated, 4 pages, Herts., England.

(List continued on next page.)

*Primary Examiner*—Arlen Soderquist
(74) *Attorney, Agent, or Firm*—Senniger, Powers, Leavitt & Roedel

(57) ABSTRACT

Computer programs and computer-implemented methods for monitoring the progress and properties of parallel chemical reactions. The invention repeatedly receives a measured value or values associated with the contents of each of a plurality of reactor vessels and displays the measured over the course of a combinatorial chemical reaction. Reaction parameters associated with individual reactor vessels are changed in response to the value measured during the reaction. Reaction parameters include temperature, pressure, stirring speed. The reaction occurring in one or more reactor vessels is quenched in response to values measured during the reaction. The measured values are used to calculate experimental results including temperature change, pressure change, percent conversion of starting material, and viscosity. The measured values and experimental results are displayed. In another aspect, the invention features a method for controlling a combinatorial chemical reactor. The method includes receiving set points for properties associated with the reaction environment in multiple reactor vessels, measuring experimental values associated with each reactor vessel, displaying the experimental values, and changing the vessels' reaction environment in response to input set points and changing experimental values. In another aspect, the invention features a reactor control system for monitoring and controlling a parallel chemical reaction. The system includes modules for providing control signals to a parallel chemical reactor, receiving measured values from the parallel chemical reactor and calculating experimental results from the measured values, and for receiving reaction parameters from the user and displaying the set of measured values and the calculated values.

46 Claims, 13 Drawing Sheets

U.S. PATENT DOCUMENTS

| | | |
|---|---|---|
| 2,996,363 A | 8/1961 | Ruyak |
| 3,143,167 A | 8/1964 | Vieth |
| 3,326,610 A | 6/1967 | Baermann et al. |
| 3,622,968 A | 11/1971 | Silverman |
| 3,676,653 A | 7/1972 | Arens et al. |
| 3,680,843 A | 8/1972 | Lu et al. |
| 3,693,941 A | 9/1972 | Suchy |
| 3,718,032 A | 2/1973 | Gray |
| 3,778,757 A | 12/1973 | Houston |
| 3,909,647 A | 9/1975 | Peterson |
| 4,106,825 A | 8/1978 | Ruyak |
| 4,151,400 A | 4/1979 | Smith et al. |
| 4,195,131 A | 3/1980 | Papas |
| 4,199,265 A | 4/1980 | Sanderson et al. |
| 4,235,592 A | 11/1980 | Smith et al. |
| 4,325,914 A | 4/1982 | Ruyak |
| 4,370,662 A | 1/1983 | Hou et al. |
| 4,391,338 A | 7/1983 | Patashnick et al. |
| 4,517,338 A | 5/1985 | Urdea et al. |
| 4,568,195 A | 2/1986 | Herz et al. |
| 4,598,049 A | 7/1986 | Zelinka et al. |
| 4,640,023 A | 2/1987 | Mori et al. |
| 4,671,941 A | 6/1987 | Niina et al. |
| 4,675,026 A | 6/1987 | Riemer et al. |
| 4,721,874 A | 1/1988 | Emmert |
| 4,741,200 A | 5/1988 | Hammerle |
| 4,746,490 A | 5/1988 | Saneii |
| 4,748,002 A | 5/1988 | Neimark et al. |
| 4,779,451 A | 10/1988 | Ezawa et al. |
| 4,858,637 A | 8/1989 | Rempel et al. |
| 4,865,986 A | 9/1989 | Coy et al. |
| 4,901,221 A | 2/1990 | Kodosky et al. |
| 4,910,523 A | 3/1990 | Huguenin et al. |
| 5,061,630 A | 10/1991 | Knopf et al. |
| 5,143,854 A | 9/1992 | Pirrung et al. |
| 5,152,488 A | 10/1992 | Richardson |
| 5,191,791 A | 3/1993 | Gerardi et al. |
| 5,201,215 A | 4/1993 | Granstaff et al. |
| 5,217,695 A | 6/1993 | Augustine et al. |
| 5,224,174 A | 6/1993 | Schneider et al. |
| 5,252,296 A | 10/1993 | Zuckermann et al. |
| 5,291,587 A | 3/1994 | Kodosky et al. |
| 5,316,728 A | 5/1994 | Hayashi et al. |
| 5,324,483 A | 6/1994 | Cody et al. |
| 5,356,756 A | 10/1994 | Cavicchi et al. |
| 5,357,964 A | 10/1994 | Spivey et al. |
| 5,367,879 A | 11/1994 | Doke et al. |
| 5,375,470 A | 12/1994 | Matsushima et al. |
| 5,380,485 A | 1/1995 | Takahashi et al. |
| 5,380,495 A | 1/1995 | Chang et al. |
| 5,395,594 A | 3/1995 | Nokihara et al. |
| 5,437,838 A | 8/1995 | DeMoranville et al. |
| 5,443,791 A | 8/1995 | Cathcart et al. |
| 5,469,369 A | 11/1995 | Rose-Pehrsson et al. |
| 5,499,193 A | 3/1996 | Sugawara et al. |
| 5,503,805 A | 4/1996 | Sugarman et al. |
| 5,515,683 A | 5/1996 | Kessler |
| 5,524,636 A | 6/1996 | Sarvazyan et al. |
| 5,538,694 A | 7/1996 | Delius |
| 5,541,314 A | 7/1996 | McGraw et al. |
| 5,544,489 A | 8/1996 | Moren |
| 5,546,301 A | 8/1996 | Agrawal et al. |
| 5,576,946 A | 11/1996 | Bender et al. |
| 5,593,642 A | 1/1997 | DeWitt et al. |
| 5,593,839 A | 1/1997 | Hubbell et al. |
| 5,601,141 A | 2/1997 | Gordon et al. |
| 5,602,756 A | 2/1997 | Atwood et al. |
| 5,609,826 A | 3/1997 | Cargill et al. |
| 5,611,059 A | 3/1997 | Benton et al. |
| 5,665,975 A | 9/1997 | Kedar |
| 5,670,269 A | 9/1997 | Hamada et al. |
| 5,698,163 A | 12/1997 | Mandel |
| 5,714,127 A | 2/1998 | DeWitt et al. |
| 5,716,584 A | 2/1998 | Baker et al. |
| 5,732,277 A | 3/1998 | Kodosky et al. |
| 5,734,098 A | 3/1998 | Kraus et al. |
| 5,746,982 A | 5/1998 | Saneii et al. |
| 5,762,881 A | 6/1998 | Harness et al. |
| 5,789,258 A | 8/1998 | Drinkwine et al. |
| 5,802,856 A | 9/1998 | Schaper et al. |
| 5,812,394 A | 9/1998 | Lewis et al. |
| 5,819,842 A | 10/1998 | Potter et al. |
| 5,841,959 A | 11/1998 | Guiremand |
| 5,856,101 A | 1/1999 | Hubbell et al. |
| 5,862,052 A | 1/1999 | Nixon et al. |
| 5,866,342 A | 2/1999 | Antonenko et al. |
| 5,888,830 A | 3/1999 | Mohan et al. |
| 5,961,925 A | 10/1999 | Ruediger et al. |
| 5,985,356 A | 11/1999 | Schultz et al. |
| 6,030,917 A | 2/2000 | Weinberg et al. |
| 6,063,633 A | 5/2000 | Willson, III |
| 6,086,831 A | 7/2000 | Harness et al. |
| 6,132,686 A | 10/2000 | Gallup et al. |

FOREIGN PATENT DOCUMENTS

| | | |
|---|---|---|
| EP | 0 635 713 A1 | 1/1995 |
| EP | 0 783 922 A1 | 7/1997 |
| EP | 0 796 654 A2 | 9/1997 |
| EP | 0 963 791 A2 | 12/1999 |
| FR | 1418757 | 10/1965 |
| FR | 2630927 | 11/1989 |
| GB | 989424 | 4/1965 |
| GB | 1408199 | 10/1975 |
| JP | 4-18424 | 1/1992 |
| JP | 10-182501 | 7/1998 |
| WO | WO 96/14930 | 5/1996 |
| WO | WO 97/09353 | 3/1997 |
| WO | WO98/07026 | 2/1998 |
| WO | WO98/13137 A1 | 4/1998 |
| WO | WO 98/13137 | 4/1998 |
| WO | WO 98/15501 A2 | 4/1998 |
| WO | WO98/15501 A2 | 4/1998 |
| WO | WO 98/15813 A1 | 4/1998 |
| WO | WO 98/39099 | 9/1998 |
| WO | WO 98/57740 | 12/1998 |
| WO | WO 99/30817 | 6/1999 |

OTHER PUBLICATIONS

Hazard Evaluation Laboratory Inc., *Hel Auto–Lab: An Automated Reactor and General Purpose Control System*, undated, 4 pages, Monmouth Junction, New Jersey, USA.

Hazard Evaluation Laboratory Inc., *Automated Batch Reactors: Bench Scale With Selected Features*, undated, 4 pages, Monmouth Junction, New Jersey, USA.

Hazard Evaluation Laboratory Inc., *HEL Newsletter*, Summer/Autumn 1993, 4 pages, Herts, England.

Hazard Evaluation Laboratory Inc., *Hel Newsletter*, Autumn/Winter 1999, 4 pages, Issue 7, Monmouth Junction, New Jersey, USA.

Hazard Evaluation Laboratory Inc., *HEL Newsletter*, Spring/Summer 2000, 4 pages, Issue 8, Monmouth Junction, New Jersey, USA.

Hazard Evaluation Laboratory Inc., *High Pressure Chem–Scan for Rapid Chemical Reaction Scanning*, undated, 2 pages, Lawrenceville, New Jersey, USA.

Hazard Evaluation Laboratory Inc., *Process Development and Safety*, undated, 5 pages, New Jersey, USA.

Hazard Evaluation Laboratory Inc., *Process Development and Safety: Using Computer Controlled Reactors and Calorimeters*, undated, 2 pages, Monmouth Junction, New Jersey, USA.

Hazard Evaluation Laboratory Inc., *Reaction Calorimetry & Laboratory Automation*, undated, 1 page, Herts., England.

Hazard Evaluation Laboratory Inc., *Reaction Calorimetry*, undated, 3 pages.

Hazard Evaluation Laboratory Inc., *Reaction Calorimetry: Simular*, undated, 2 pages, Monmouth Junction, New Jersey, USA.

Hazard Evaluation Laboratory Inc., *Research Scale Reactor Automation: Auto–MATE*, undated, 4 pages, Monmouth Junction, New Jersey, USA.

Hazard Evaluation Laboratory Inc., *Introducing Tips: Tools for Integration of Process Systems*, undated, 1 page, New Jersey, USA.

Hazard Evaluation Laboratory Inc., *Miniature Multiple Reactor System: auto–MATE*, undated, 8 pages, Monmouth Junction, New Jersey, USA.

Hazard Evaluation Laboratory Inc., *Specify SIMULAR Around Your Chemistry*, undated, 5 pages, Lawrenceville, New Jersey, USA.

Hazard Evaluation Laboratory Inc., *First Amended Complaint with Jury Demand*, Jul. 31, 2002, 5 pages, New Jersey, USA.

Hazard Evaluation Laboratory Inc., *Answer to Counterclaim*, Sep. 9, 2002, 3 pages, New Jersey, USA.

Singh, Jasbir, et al, *Thermal Analysis and Reaction Calorimetry*, undated, 3 pages.

Scientific Update, *The Evolution of a Revolution: Laboratory Automation in Chemical Process R&D*, Sep. 5, 1997, 3 pages, East Sussex, United Kingdom.

Singh, Jasbir, *Assessing Semi–Batch Reaction Hazards*, The Chemical Engineer, Feb. 25, 1993, 4 pages.

Singh, Jasbir, *Reaction Calorimetry for Process Development: Recent Advances*, Process Safety Progress, Spring 1997, 7 pages.

Singh, Jasbir, *Automation of Reaction Research—An Alternative to Robotics*, European Pharmaceutical Contractor, Nov. 1997, 4 pages.

Singh, Jasbir, *Safe Scaleup of Exothermic Reactions*, Chemical Engineering, May 1997, 4 pages.

Singh, Jasbir, *Scaleable Automated Laboratory Reactors*, undated ("Scaleable Automated Laboratory Reactors" title listed in reference 179 noted above), 13 pages, East Sussex, United Kingdom.

Parr Instrument Company, *Stirred Reactors: Series 4520 Options*, undated, 3 pages.

SYMYX Technologies, Inc., Answer and Counterclaim, Aug. 30, 2002, 8 pages, New Jersey, USA.

SYMYX Technologies, Inc., First Amended Answer and Counterclaim, Oct. 30, 2002, 9 pages, New Jersey, USA.

Hazard Evaluation Laboratory Inc., Untitled Drawings, undated, 4 pages.

Waldram, Simon, et al., *Increasing the Scale of Process Operations: How to Identify Exothermic Reaction Hazards*, undated, 3 pages.

Cargill, J. et al., "Automated Combinatorial Chemistry on Solid Phase," Laboratory Robotics and Automation, Mar. 21, 1996, vol. 8, pp. 139–148, John Wiley & Sons, Inc., New York, New York, US.

Takamatsu, T., et al., "Optimal Scheduling and Minimum Storage Tank Capacities in a Process System with Parallel Batch Units," Comput. Chem. Eng. 1973, 3, 185–195.

Gehrer, E., et al., "A Fully Programmable System for the Study of Catalytic Gas Reactions," J. Phys. E: Sci. Instrum. 1985, 18, 10, 836–838.

McFarlane, R.C., et al., "Adaptive Optimizing Control of Multivariable Constrained Chemical Processes. 2. Application Studies," Ind. Eng. Chem. Res. 1989, 28, 1834–1845.

Josses, P., et al., "Carrying Out Multiple Reactions in Organic Synthesis with a Robot," Adv. Lab. Autom. Rob. 1990, 6, 463–475.

Corkan, A., et al., "Design Concepts for Synthetic Chemistry Workstations," Adv. Lab. Autom. Rob. 1990, 6, 477–497.

Li, K.T., et al., Mixing and Control of a CSTR with Series–Parallel Reactions, J. Chin. Inst. Chem. Eng. 1991, 22, 61–69.

Lindsey, J.S., A Retrospective on the Automation of Laboratory Synthetic Chemistry, Chemom. Intell. Lab. Syst. 1992, 17, 15–45.

Plouvier, J.C., et al., "Experiment Planner for Strategic Experimentation with an Automated Chemistry Workstation," Chemom. Intell. Lab. Syst. 1992, 17–75–94.

Corkan, L.A., et al., "Application of an Automated Chemistry Workstation to Problems in Synthetic Chemistry," Chemom. Intell. Lab. Syst. 1992, 17 95–105.

Buhlmann, R., et al., "An Open Software Environment to Optimize the Productivity of Robotized Laboratories," J. Chromatogr. Sci. 1994, 32, 243–248.

Tietze, A., et al., "Temperature Oscillation Calorimetry in Stirred Tank Polymerization Reactors," DECHEMA Monogr. 1995, 131, 673–680.

Ahrweiler, P. et al., "Automation of Parallel Synthesis From Reagent Preparation Through Sample Workup," Am. Lab. 1997, 29, 12–14.

S. Vignes et al, Comp. Rend. Congr. Indust. 1961, 405–411.

L. Kiezel et al, Chem. Stosow, 1968, 12, 407–415.

J. Nelles et al, Chem. Tech. 1975, 27, 714–716.

J. F. Cargill et al, Lab. Rob. Autom. 1996, 8, 139–148.

M. Salvet et al, Chem. Abstr. 1997, 126, abstract 200993h.

"Applications of the Piezoelectric Crystal Detector in Analytical Chemistry," J. Hlavay and G.G. Gullbault, *Analytical Chemistry*, vol. 49, No. 13, Nov. 1977.

"Electrolytic Determination of Nanomolar Concentrations of Silver in Solution with a Piezoelectric Quartz Crystal," T. Nomura and M. Iijima, *Analytica Chemica Acta*, vol. 131, pp. 97–102, 1981.

"The Oscillation Frequency of a Quartz Resonator in Contact with a Liquid," K. Keiji Kanazawa and Joseph G. Gordon, II, *Analytica Chemica Acta*, vol. 175, pp. 99–105, 1985.

"Computation of Equivalent Circuit Parameters of Quartz Crystals in Contact with Liquids and Study of Liquid Properties, Hiroshi Muramatsu," Eiichi Tamiya and Isao Karube, *Analytical Chemistry*, vol. 60, pp. 2142–2146, 1988.

"Network Analysis Method Applied to Liquid–Phase Acoustic Wave Sensors," *Analytical Chemistry*, A.L. Kipling, M. Thomson, pp. 1514–1519, vol. 62, 1990.

"A Quartz Crystal Viscosity Sensor for Monitoring Coagulation Reaction and Its Application to a Multichannel Coagulation Detector," H. Muramatsu, K. Kumura, T. Ataka, R. Homma, Y. Miura and I. Karube, *Biosensors & Bioelectronics*, vol. 6, pp. 353–358, 1991.

"Experimental Manager Software for an Automated Chemistry Workstation, Including a Scheduler for Paralled Experimentation," Corkan, et al, *Chemometrics and Intelligent Laboratory Systems: Laboratory Information Management*, 17 (1992) Oct., No. 1,47–74.

1 MHz quartz length extension resonator as a probe for scanning near–field acoustic microscopy, *Thin Solid Films*, A. Michels, F. Meinen, T. Murdfield, W. Gohde, U.C. Fischer, E. Beckmann and H. Fuchs, vol. 264, pp. 172–195, 1995.

"Heated Reacto—Stations," Estem Corporation, Oct. 1997.

"Microreactor Technology: Focusing the German Activities in this Novel and Promising Field of Chemical Process Engineering," J.P. Baselt, A. Forster, J. Herrmann, and D. Tiebes, pp. 13–17, 1997.

World Wide Web brinkmann.com 1997 "Brinkmann Horizon Stirrers and Hotplace Stirrers" information.

World Wide Web calbay.com Mar. 31, 1998 "Viscoliner" information.

World Wide Web argotech.com/quest May 18, 1998 "Nautilus 2400" information.

World Wide Web argotech.com/quest May 18, 1998 "QUEST 210" information.

World Wide Web tecan.ch Jul. 14, 1998 "CAVRO RSP 9000 Robotic Sample Processor" information.

World Wide Web thermometric.com/calorimetry Jul. 27, 1998 "Caloimetry" information.

World Wide Web mettler.com Aug. 10, 1998 "Automated Laboratory Reactors, Reaction Calorimeters and On–line Analysis" information.

World Wide Web calscorp.com/about_csc Feb. 8, 1999 "About Calorimetry Sciences Corp." information.

"MultiReactor—Reactor Block," RoboSynthon, Inc.

J–KEM © Scientific, Inc. "Reaction Blocks" information.

ANALYSIS AND CONTROL OF PARALLEL CHEMICAL REACTIONS

This application is a divisional of prior Ser. No. 09/239,223, filed Jan. 29, 1999, now U.S. Pat. No. 6,489,168, which is a continuation-in-part of Ser. No. 09/211,982, filed Dec. 14, 1998, now U.S. Pat. No. 6,306,658, which is a continuation-in-part of Ser. No. 09/177,170, filed Oct. 22, 1998, now U.S. Pat. No. 6,548,026, which claims the benefit of provisional Ser. No. 60/096,603, filed Aug. 13, 1998.

BACKGROUND OF THE INVENTION

The present invention relates to methods and computer programs for rapidly screening and characterizing an array of materials.

In combinatorial chemistry, a large number of candidate materials are created from a relatively small set of precursors and subsequently evaluated for suitability for a particular application. As currently practiced, combinatorial chemistry permits scientists to explore systematically the influence of structural variations in candidates by dramatically accelerating the rates at which they are created and evaluated. Compared to traditional discovery methods, combinatorial methods sharply reduce the costs associated with preparing and screening each candidate.

Combinatorial chemistry has revolutionized the process of drug discovery. One can view drug discovery as a two-step process: acquiring candidate compounds through laboratory synthesis or through natural products collection, followed by evaluation or screening for efficacy. Pharmaceutical researchers have long used high-throughput screening (HTS) protocols to rapidly evaluate the therapeutic value of natural products and libraries of compounds synthesized and cataloged over many years. However, compared to HTS protocols, chemical synthesis has historically been a slow, arduous process. With the advent of combinatorial methods, scientists can now create large libraries of organic molecules at a pace on par with HTS protocols.

Recently, combinatorial approaches have been used for discovery programs unrelated to drugs. For example, some researchers have recognized that combinatorial strategies also offer promise for the discovery of inorganic compounds such as high-temperature superconductors, magnetoresistive materials, luminescent materials, and catalytic materials. See, for example, co-pending U.S. patent application Ser. No. 08/327,513 "The Combinatorial Synthesis of Novel Materials" (published as WO 96/11878) and co-pending U.S. patent application Ser. No. 08/898,715 "Combinatorial Synthesis and Analysis of Organometallic Compounds and Catalysts" (a version of which has been published as WO 98/03251), which are all incorporated herein by reference.

SUMMARY OF THE INVENTION

The present invention provides computer programs and computer-implemented methods for monitoring the progress and properties of parallel chemical reactions.

In general, in one aspect, the invention features a method of monitoring a combinatorial chemical reaction. The method includes (a) receiving a measured value associated with the contents of each of a plurality of reactor vessels; (b) storing the measured values in a memory; and (c) repeating steps (a) and (b) multiple times over the course of the combinatorial chemical reaction.

Implementations of the invention can include one or more of the following advantageous features. The measured values include a set of values for a number of reaction conditions associated with each of the reactor vessels. Step (c) is performed at a predetermined sampling rate. The method also includes changing a reaction parameter associated with one of the reactor vessels in response to the measured value to maintain the reactor vessel at a predetermined set point, the reaction condition is temperature. The reaction condition is pressure. The reaction condition is motor speed. The method also includes quenching a catalyst in one of the reactor vessels in response to the measured value associated with the contents of the reactor vessel. The method also includes using the measured value to calculate an experimental value for one of the reactor vessels. The experimental variable is a change in temperature. The experimental variable is a change in pressure. The experimental variable is percent conversion of starting material. The experimental variable is viscosity. The method also includes displaying the experimental variable.

In general, in another aspect, the invention features a method for controlling a combinatorial chemical reactor including multiple reactor vessels, each containing a reaction environment. The method includes receiving a set point for a property associated with each vessel's reaction environment; measuring a set of experimental values for the property for each vessel; storing the set of experimental values in a memory; and changing the reaction environment in one or more of the plurality of reactor vessels in response to the set point and a change in one or more of the set of experimental values.

Implementations of the invention can include one or more of the following advantageous features. Changing the reaction environment includes terminating a reaction occurring in a reactor vessel, the set point is a conversion target, and the change in an experimental value is a change in percent conversion of starting material. A graphical representation of the set of experimental values is displayed. The graphical representation is a histogram.

In general, in another aspect, the invention features a computer program on a computer-readable medium for monitoring a combinatorial chemical reaction. The program includes instructions to (a) receive a measured value associated with the contents of each of a plurality of reactor vessels; (b) store the measured values in a memory, and (c) repeat steps (a) and (b) multiple times during the course of the combinatorial chemical reaction.

Implementations of the invention can include one or more of the following advantageous features. The computer program includes instructions to change a reaction parameter associated with one of the reactor vessels in response to the measured value to maintain the reactor vessel at a predetermined set point.

In general, in another aspect, the invention features a reactor control system for monitoring and controlling parallel chemical reactions. The reactor system includes a control providing control signals to a parallel chemical reactor including multiple reactor vessels; an analyzer receiving a set of measured values from the parallel chemical reactor and calculating one or more calculated values for each of the reactor vessels; and a user interface for receiving at least one of the reaction parameters and displaying at least one of the set of measured values and the calculated values.

Advantages that can be seen in implementations of the invention include one or more of the following. Process variables can be monitored and controlled for multiple elements in a combinatorial library as a chemical reaction progresses. Data can be extracted for each library element repeatedly and in parallel over the course of the reaction, instead of extracting only a limited number of data points for selected library elements. Calculations and corrections can be applied automatically to every available data point for every library element over the course of the reaction. A single experimental value can be calculated from the entire data set for each library element.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

The present invention provides computer programs and computer-implemented methods for monitoring the progress and properties of multiple reactions in situ. It is especially useful for screening and characterizing combinatorial libraries, but offers significant advantages over conventional experimental reactor control and data analysis techniques as well. For example, in situ monitoring of individual reaction mixtures not only provides feedback for process controllers, but also provides data for determining reaction rates, product yields, and various properties of the reaction products, including viscosity and molecular weight, while the experiment is in progress. Moreover, in situ monitoring coupled with tight process control can improve product selectivity, provide opportunities for process and product optimization, allow processing of temperature-sensitive materials, and decrease experimental variability.

Figure 1:
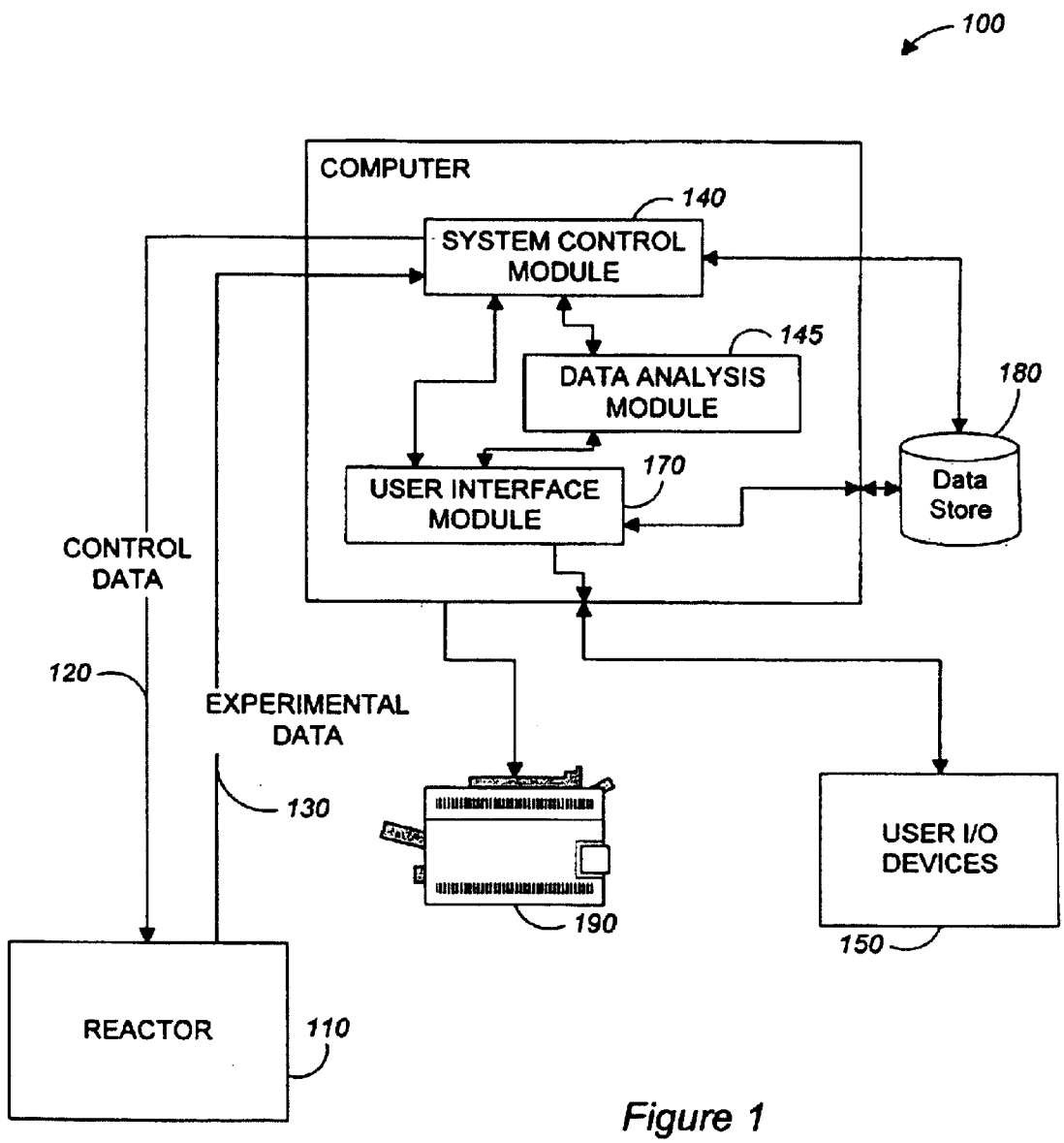
FIG. 1 is a block diagram of a data processing system showing an implementation of the invention.

One implementation of the invention is illustrated in FIG. 1. Reactor control system 100 sends control data 120 to and receives experimental data 130 from reactor 110. As will be described in more detail below, in one embodiment reactor 110 is a parallel polymerization reactor and the control and experimental data 120 and 130 include set point values for temperature, pressure, time and stirring speed as well as measured experimental values for temperature and pressure. Alternatively, in other embodiments reactor 110 can be any other type of parallel reactor or conventional reactor, and data 120, 130 can include other control or experimental data. System control module 140 provides reactor 110 with control data 120 based on system parameters obtained from the user through user I/O devices 150, such as a display monitor, keyboard or mouse. Alternatively, system control module 140 can retrieve control data 120 from storage 180.

Reactor control system 100 acquires experimental data 130 from reactor 110 and processes the experimental data in system control module 140 and data analysis module 145 under user control through user interface module 170. Reactor control system 100 displays the processed data both numerically and graphically through user interface module 170 and user I/O devices 150, and optionally through printer 190.

Parallel Polymerization Reactor Control and Analysis

Figure 2A:
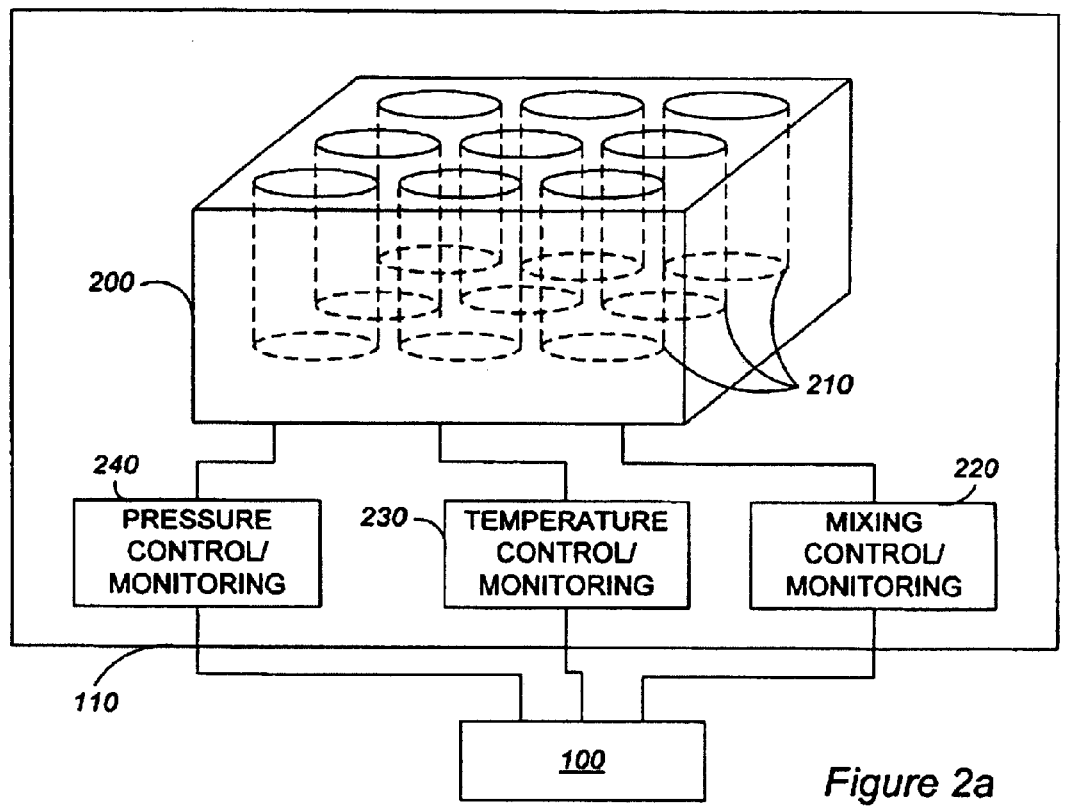
FIGS. 2a–2d are schematic diagrams of a parallel reactor suitable for use with the invention.

FIG. 2a illustrates one embodiment of reactor 110 in more detail. Reactor 110 includes reactor block 200, which contains sealed reactor vessels 210 for receiving reagents. In one embodiment, reactor block 200 is a single unit containing each of reactor vessels 210. Alternatively, reactor block 200 can include a number of reactor block modules, each of which contains a number of reactor vessels 210. Reactor 110 includes a mixing control and monitoring system 220, a temperature control and monitoring system 230 and a pressure control and monitoring system 240. These systems communicate with reactor control system 100.

Figure 2B:
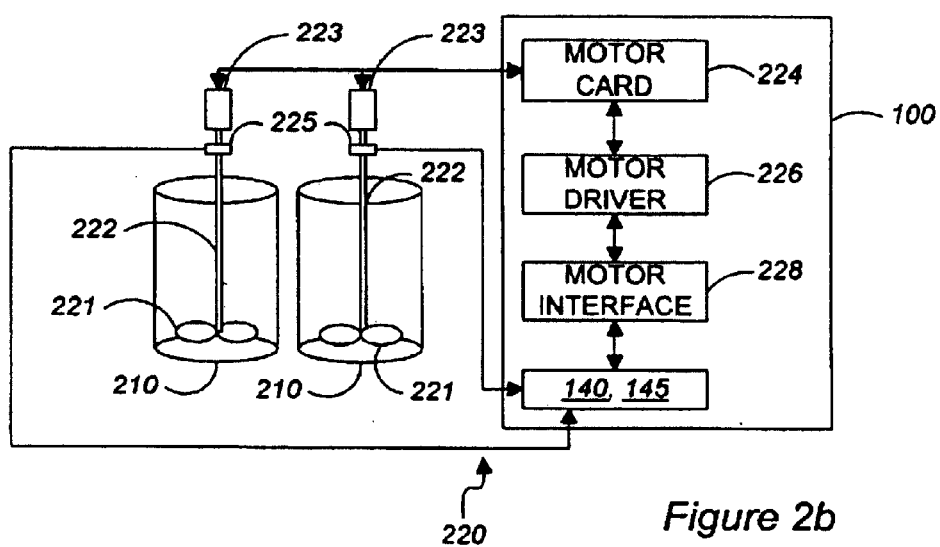

The details of mixing control and monitoring system 220 are illustrated in FIG. 2b. Each of reactor vessels 210 contains a stirrer 221 for mixing the vessel contents. In one embodiment, stirrers 221 are stirring blades mounted on spindles 222 and driven by motors 223. Separate motors 223 can control each individual stirrer 221; alternatively, motors 223 can control groups of stirrers 221 associated with reactor vessels 210 in separate reactor blocks. In another embodiment, magnetic stirring bars or other known stirring mechanisms can be used. System control module 140 provides mixing control signals to stirrers 221 through interface 226, 228, and one or more motor cards 224. Interface 226, 228 can include a commercial motor driver 226 and motor interface software 228 that provides additional high level motor control, such as the ability to initialize motor cards 224, to control specific motors or motor axes (where each motor 224 controls a separate reactor block), to set motor speed and acceleration, and to change or stop a specified motor or motor axis.

Mixing control and monitoring system 220 can also include torque monitors 225, which monitor the applied torque in each of reactor vessels 210. Suitable torque monitors 225 can include optical sensors and magnetic field sensors mounted on spindles 222, or strain gauges (not shown), which directly measure the applied torque and transmit torque data to system control module 140 and data analysis module 145. Monitors 225 can also include encoders, resolvers, Hall effect sensors and the like, which may be integrated into motors 223. These monitors measure the power required to maintain a constant spindle 222 rotational speed, which is related to applied torque.

Figure 2C:
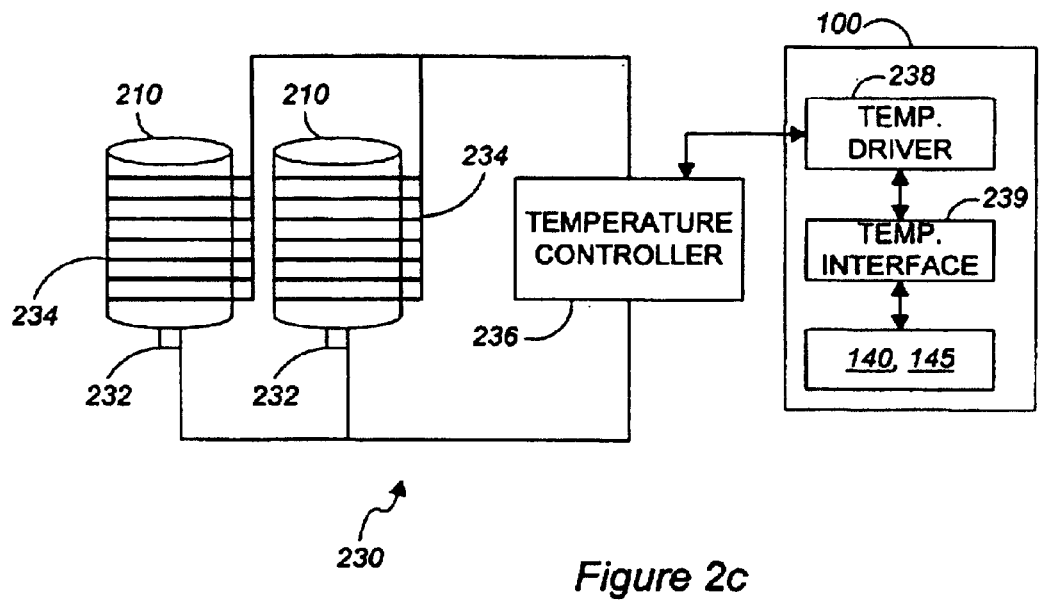

Referring to FIG. 2c, temperature control and monitoring system 230 includes a temperature sensor 232 and a heating element 234 associated with each reactor vessel 210 and controlled by temperature controller 236. Suitable heating elements 234 can include thin filament resistance heaters, thermoelectric devices, thermistors, or other devices for regulating vessel temperature. Heating elements can include devices for cooling, as well as heating, reactor vessels 210. System control unit 140 transmits temperature control signals to heating elements 234 through interface 238, 239 and temperature controller 236. Interface 238, 239 can include a commercial temperature device driver 238 implemented to use hardware such as an RS232 interface, and temperature interface software 239 that provides additional high level communication with temperature controller 236, such as the ability to control the appropriate communication port, to send temperature set points to temperature controller 236, and to receive temperature data from temperature controller 236.

Suitable temperature sensors 232 can include thermocouples, resistance thermoelectric devices, thermistors, or other temperature sensing devices. Temperature controller 236 receives signals from temperature sensors 232 and transmits temperature data to reactor control system 100. Upon determining that an increase or decrease in reactor vessel temperature is appropriate, system control module 140 transmits temperature control signals to heating elements 234 through heater controller 236. This determination can be based on temperature parameters entered by the user through user interface module 170, or on parameters retrieved by system control module 140 from storage. System control module 140 can also use information received from temperature sensors 232 to determine whether an increase or decrease in reactor vessel temperature is necessary.

Figure 2D:
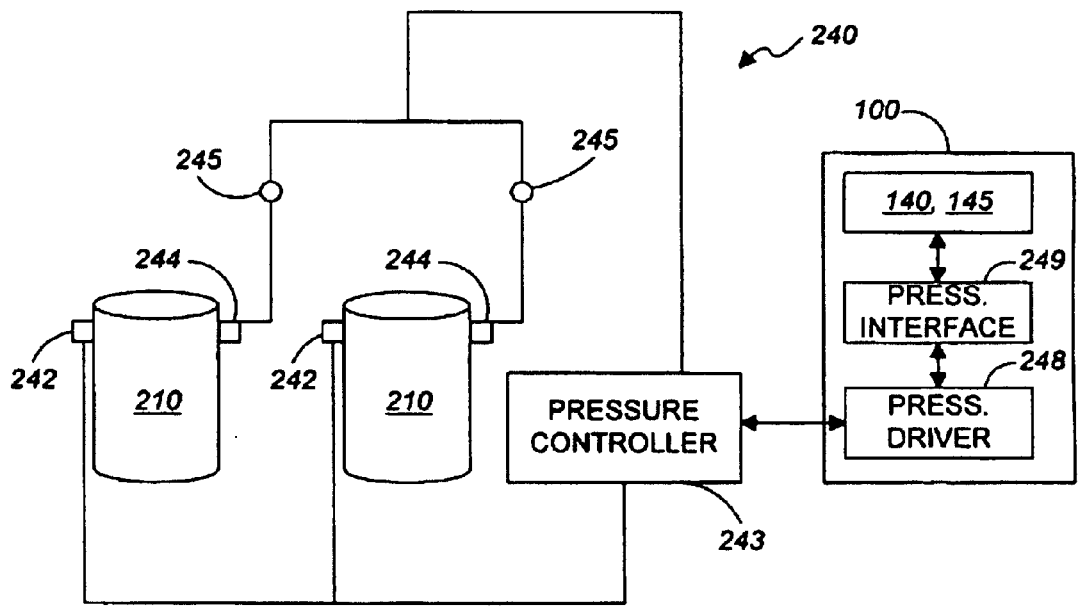

As shown in FIG. 2d, pressure control and monitoring system 240 includes a pressure sensor 242 associated with each reactor vessel 210. Each reactor vessel 210 is furnished with a gas inlet/outlet 244 that is controlled by valves 245. System control module 140 controls reactor vessel pressure through pressure interface 248, 249 and pressure controller 243. Pressure interface 248, 249 can be implemented in hardware, software or a combination of both. Pressure controller 243 transmits pressure control signals to valves 245 allowing gases to enter or exit reactor vessels 210 through inlet/outlet 244 as required to maintain reactor vessel pressure at a level set by the user through user interface 170.

Pressure sensors 242 obtain pressure readings from reactor vessels 210 and transmit pressure data to system control module 140 and data analysis module 145 through pressure controller 243 and interface 248, 249. Data analysis module 145 uses the pressure data in calculations such as the determination of the rate of production of gaseous reaction products or the rate of consumption of gaseous reactants, discussed in more detail below. System control module 140 uses the pressure data to determine when adjustments to reactor vessel pressure are required, as discussed above.

Figure 3:
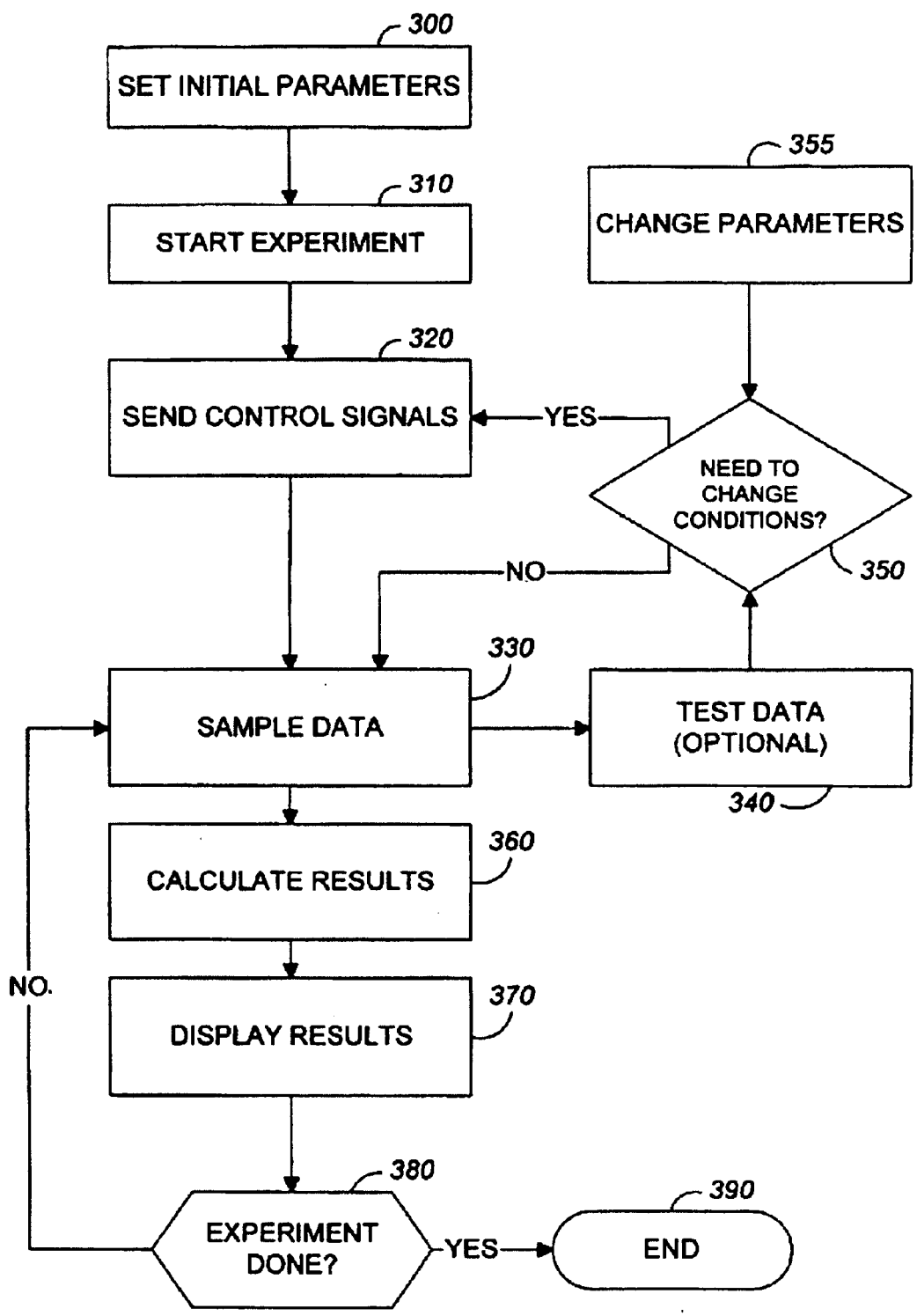
FIG. 3 is a flow diagram of a method of controlling and analyzing a parallel chemical reaction.

FIG. 3 is a flow diagram illustrating the operation of a reactor control system 100. The user initializes reactor control system 100 by setting the initial reaction parameters, such as set points for temperature, pressure and stirring speed and the duration of the experiment, as well as selecting the appropriate hardware configuration for the experiment (step 300). The user can also set other reaction parameters that can include, for example, a time at which additional reagents, such as a liquid co-monomer in a co-polymerization experiment, should be added to reaction vessels 210, or a target conversion percentage at which a quenching agent should be added to terminate a catalytic polymerization experiment. Alternatively, reactor control system 100 can load initial parameters from storage 180. The user starts the experiment (step 310). Reactor control system 100 sends control signals to reactor 110, causing motor, temperature and pressure control systems 220, 230 and 240 to bring reactor vessels 210 to set point levels (step 320).

Reactor control system 100 samples data through mixing monitoring system 220, temperature monitoring system 230 and pressure monitoring system 240 at sampling rates, which may be entered by the user (step 330). Reactor control system 100 can provide process control by testing the experimental data, including sampled temperature, pressure or torque values as well as elapsed time, against initial parameters (step 340). Based on these inputs, reactor control system 100 sends new control signals to the mixing, temperature and/or pressure control and monitoring systems of reactor 110 (steps 350, 320). These control signals can also include instructions to a material handling robot to add material, such as a reagent or a catalyst quenching agent, to one or more reactor vessels based upon experimental data such as elapsed time or percent conversion calculated as discussed below. The user can also enter new parameters during the course of the experiment, such as changes in motor speed, set points for temperature or pressure, or termination controlling parameters such as experiment time or percent conversion target (step 355), which may also cause reactor control system 100 to send new control signals to reactor 110 (steps 355, 350, 320).

Data analysis module 145 performs appropriate calculations on the sampled data (step 360), as will be discussed below, and the results are displayed on monitor 150 (step 370). Calculated results and/or sampled data can be stored in data storage 180 for later display and analysis. Reactor control system 100 determines whether the experiment is complete—for example, by determining whether the time for the experiment has elapsed (step 380). Reactor control system 100 can also determine whether the reaction occurring in one or more of reactor vessels 210 has reached a specified conversion target based on results calculated in step 360; in that case, reactor control system 100 causes the addition of a quenching agent to the relevant reactor vessel or vessels as discussed above, terminating the reaction in that vessel. For any remaining reactor vessels, reactor control system 100 samples additional data (step 330) and the cycle begins anew. When all reactor vessels 210 in reactor block 200 have reached a specified termination condition, the experiment is complete (step 390). The user can also cause the reaction to terminate by aborting the experiment at any time. It should be recognized that the steps illustrated in FIG. 3 are not necessarily performed in the order shown; instead, the operation of reactor control system 100 can be event driven, responding, for example, to user events, such as changes in reaction parameters, or system generated periodic events.

Analysis of Experimental Data

The type of calculation performed by data analysis module 145 (step 360) depends on the nature of the experiment. As discussed above, while an experiment is in progress, reactor control system 100 periodically receives temperature, pressure and/or torque data from reactor 10 at sampling rates set by the user (step 330). System control module 140 and data analysis module 145 process the data for use in screening materials or for performing quantitative calculations and for display by user interface module 170 in formats such as those shown in FIGS. 7a–7b and 8.

Reactor control system 100 uses temperature measurements from temperature sensors 232 as a screening criteria or to calculate useful process and product variables. For instance, in one implementation, catalysts of exothermic reactions are ranked based on peak reaction temperature reached within each reactor vessel, rates of change of temperature with respect to time, or total heat released over the course of reaction. Typically, the best catalysts of an exothermic reaction are those that, when combined with a set of reactants, result in the greatest heat production in the shortest amount of time. In other implementations, reactor control system 100 uses temperature measurements to compute rates of reaction and conversion.

In addition to processing temperature data as a screening tool, in another implementation, reactor control system 100 uses temperature measurement—combined with proper thermal management and design of the reactor system—to obtain quantitative calorimetric data. From such data, reactor control system 100 can, for example, compute instantaneous conversion and reaction rate, locate phase transitions (e.g., melting point, glass transition temperature) of reaction products, or measure latent heats to deduce structural information of polymeric materials, including degree of crystallinity and branching.

Calorimetric data can be obtained using a reactor 200 made of a material having high thermal conductivity, such as aluminum, stainless steel or brass. High thermal conductivity, accompanied by active heating or cooling using any of the methods described above, help maintain a uniform temperature $T_o$ throughout the reactor block 200. Reactor vessels 210 are generally made of a material having relatively low thermal conductivity and are insulated to further decrease heat transfer to or from the vessels. Each vessel contains stirring blades 221 to ensure that the contents of the vessels 210 are well mixed and that the temperature within any one of the vessels 210, $T_j$, is uniform. Each of the vessels contains a thermistor, which serves as a temperature sensor 232, measuring temperature $T_j$, and a heating element 234 to heat the vessel contents. One can account for non-uniform temperatures within the reactor block 200 by measuring $T_{oj}$, the temperature of the block 200 in the vicinity of each of the vessels 210, using block temperature sensors. In such cases, $T_{oj}$, instead of $T_o$, is used in the calorimetric calculations described next.

An energy balance around the contents of one of the vessels 210 (jth vessel) yields an expression for fractional conversion $X_j$ of a key reactant at any time t, assuming that the heat of reaction $\Delta H_{rj}$ and the specific heat of the vessel contents $C_{Pj}$ are known and are constant over the temperature range of interest:

$$M_j c_{p,j} \frac{dT_j}{dt} = m_{o,j}\Delta H_{r,j}\frac{dX_j}{dt} + Q_{inj} - Q_{outj}. \quad \text{(Eq. 1)}$$

In Equation 1, $M_j$ is the mass of the contents of the jth vessel; $m_{oj}$ is the initial mass of the key reactant; and $Q_{inj}$ is the rate of heat transfer into the jth vessel by processes other than reaction, as for example, by resistance heating of the thermistor. $Q_{outj}$ is the rate of heat transfer out of the jth vessel, which can be determined from the expression:

$$Q_{outj}=U_j A_j(T_j-T_o)=U_j A_j \Delta T_j \quad \text{(Eq. 2)}$$

where $A_j$ is the heat transfer area—the surface area of the jth vessel—and $U_j$ is the heat transfer coefficient, which depends on the properties of the vessel 210 and its contents, as well as the stirring rate. $U_j$ can be determined by measuring the temperature rise $\Delta T_j$ in response to a known heat input.

Reactor control system 100 can use Equations 1 and 2 to determine conversion from calorimetric data in at least two ways. In a first method, the temperature of the reactor block 200 is held constant, and sufficient heat is added to each of the vessels 210 through thermistor 234 to maintain a constant value of $\Delta T_j$. Under such conditions, and after combining Equations 1 and 2, the conversion can be calculated from the expression $$X_j = \frac{1}{m_{o,j}\Delta H_{r,j}}\left(U_j A_j t_j \Delta T_j - \int_0^{t_f} Q_{inj}\,dt\right), \quad \text{(Eq. 3)}$$

where the integral can be determined by numerically integrating the power consumption of the thermistor 234 over the length of the experiment $t_f$. In this implementation, reactor control system 100 method determines the heat output of a reaction under isothermal conditions.

In a second implementation, the temperature of the reactor block 200 is again held constant, but $T_j$ increases or decreases in response to heat produced or consumed in the reaction. Equations 1 and 2 become under such circumstances $$X_j = \frac{1}{m_{o,j}\Delta H_{r,j}}\left(M_j c_{p,j}\left(T_{f,j}-T_{i,j}+U_f A_f \int_0^{t_f}\Delta T_j\,dt\right)\right). \quad \text{(Eq. 4)}$$

In Equation 4, the integral can be determined numerically, and $T_{fj}$ and $T_{ij}$ are temperatures of the reaction mixture within the jth vessel at the beginning and end of reaction, respectively. Thus, if $T_{fj}$ equals $T_{ij}$, the total heat liberated is proportional to $$\int_0^{t_f}\Delta T_j\,dt.$$

This method is simpler to implement than the isothermal method since it does not require temperature control of individual vessels. However, it can be used only when the temperature change in each of the reaction vessels 210 due to reaction does not significantly influence the reaction under study.

In another implementation, reactor control system 100 calculates the instantaneous rate of disappearance of the key reactant in the jth vessel, $-r_j$, using Equations 1, 3 or 4 because $-r_j$ is related to conversion through the relationship $$-r_j = C_{o,j}\frac{dX_j}{dt}, \quad \text{(Eq. 5)}$$

which is valid for constant volume reactions. The constant $C_{oj}$ is the initial concentration of the key reactant.

Reactor control system 100 can also monitor mixing variables such as applied stirring blade torque in order to determine the viscosity of the reaction mixture and related properties. Reactor control system 100 can use such data to monitor reactant conversion and to rank or characterize materials based on molecular weight or particle size.

The viscosity of a polymer solution depends on the molecular weight of the polymer and its concentration in solution. For polymer concentrations well below the "semi-dilute limit"—the concentration at which the solvated polymers begin to overlap one another—the solution viscosity η is related to the polymer concentration C in the limit as C approaches zero by the expression $$\eta=(1+C[\eta])\eta_s \quad \text{(Eq. 6)}$$

where $\eta_s$ is the viscosity of the solvent. Essentially, adding polymer to a solvent increases the solvent's viscosity by an amount proportional to the polymer concentration. The proportionality constant [η] is known as the intrinsic viscosity and is related to the polymer molecular weight M through the expression $$[\eta]=[\eta_o]M_\alpha, \quad\quad\quad\quad\quad\quad\quad\quad\quad\quad (Eq. 7)$$

where $[\eta_o]$ and a are empirical constants. In one implementation, reactor control system 100 uses Equation 7, known as the Mark-Houwink-Sakurda (MHS) relation, along with Equation 6, to determine molecular weight from viscosity measurements.

Equation 6 requires concentration data from another source; with polymerization reactions, polymer concentration is directly related to monomer conversion. Reactor control system 100 obtains such data by measuring heat evolved during reaction (see Equations 3 and 4) or, as described below, by measuring the amount of a gaseous reactant consumed during reaction. The constants in the MHS relation are functions of temperature, polymer composition, polymer conformation, and the quality of the polymer-solvent interaction. The empirical constants $[\eta_o]$ and α have been measured for a variety of polymer-solvent pairs and are tabulated in the literature.

Although Equations 6 and 7 can be used to approximate molecular weight, reactor control system 100 uses in situ measurements of viscosity mainly to rank reaction products as a function of molecular weight. Under many circumstances, the amount of solvent necessary to satisfy the concentration requirement of Equation 6 would slow the rate of reaction to an unacceptable level. Therefore, polymerizations are generally carried out at polymer concentrations above the semidilute limit, where the use of Equations 6 and 7 to calculate molecular weight would lead to large error. Nevertheless, reactor control system 100 can use viscosity to rank reaction products even at concentrations above the semidilute limit because a rise in viscosity during reaction generally reflects an increase in polymer concentration, molecular weight or both. If necessary, one can accurately determine molecular weight from viscosity measurements at relatively high polymer concentration by first preparing temperature-dependent calibration curves that relate viscosity to molecular weight for every polymer-solvent pair produced.

In addition to ranking reactions, in other implementations reactor control system 100 uses viscosity measurements to screen or characterize dilute suspensions of insoluble particles—polymer emulsions or porous supports for heterogeneous catalysts—in which viscosity increases with particle size at a fixed concentration. In the case of polymer emulsions, viscosity can serve as a measure of emulsion quality. For example, solution viscosity that is constant over long periods of time may indicate superior emulsion stability, or viscosity within a particular range may correlate with a desired emulsion particle size. With porous supports, viscosity measurements can be used to identify active catalysts: in many cases, the catalyst support will swell during reaction due to the formation of insoluble products within the porous support.

Viscosity or related properties of the reactant mixtures are monitored by measuring the effect of viscous forces on stirring blade rotation. Viscosity is a measure of a fluid's resistance to a shear force. This shear force is equal to the applied torque Γ needed to maintain a constant angular velocity of the stirring blade. The relationship between the viscosity of the reaction mixture and the applied torque can be expressed as $$\Gamma=K_\omega(\omega,T)\eta, \quad\quad\quad\quad\quad\quad\quad\quad\quad\quad (Eq. 8)$$

where $K_\omega$ is a proportionality constant that depends on the angular frequency ω of the stirring bar, the temperature of the reaction mixture, and the geometries of the reaction vessel and the stirring blade. $K_\omega$ can be obtained through calibration with solutions of known viscosity.

During a polymerization reaction, the viscosity of the reaction mixture increases over time due to the increase in molecular weight of the reaction product or polymer concentration or both. Reactor control system 100 monitors this change in viscosity by measuring the applied torque and using Equation 8 to convert the measured data to viscosity. In many instances, actual values for the viscosity are unnecessary, and one can dispense with the conversion step. For example, in situ measurements of applied torque can be used to rank reaction products based on molecular weight or conversion, as long as stirring rate, temperature, vessel geometry and stirring blade geometry are about the same for each reaction mixture.

In addition to direct measurement, reactor control system 100 can determine torque indirectly by measuring the phase angle or phase lag between the stirring blade and the driving force or torque. Indirect measurement requires that the coupling between the driving torque and the stirring blade is soft, so that significant and measurable phase lag occurs.

With magnetic stirring, soft coupling occurs automatically. The torque on the stirring bar is related to the magnetic moment of the stirring bar, μ, and the amplitude of the magnetic field that drives the rotation of the stirring bar, H, through the expression $$\Gamma=\mu H \sin\theta, \quad\quad\quad\quad\quad\quad\quad\quad\quad\quad (Eq. 9)$$

where θ is the angle between the axis of the stirring bar (magnetic moment) and the direction of the magnetic field. At a given angular frequency, and for known μ and H, the phase angle θ will automatically adjust itself to the value necessary to provide the amount of torque needed at that frequency. If the torque required to stir at frequency ω is proportional to the solution viscosity and the stirring frequency—a useful approximation—the viscosity can be calculated from measurements of the phase angle using the equation $$\Gamma=\mu H \sin\theta=\alpha\eta\omega \quad\quad\quad\quad\quad\quad\quad\quad\quad\quad (Eq. 10)$$

where α is a proportionality constant that depends on temperature and on the geometry of the vessel and the stirring blade. In practice, one may use Equation 8 or a similar empirical expression for the right hand side of Equation 10 if the torque does not depend linearly on the viscosity-frequency product.

Reactor control system 100 can also assess reaction kinetics by monitoring pressure changes due to production or consumption of various gases during reaction. Reactor control system 100 uses pressure sensors 242 to measure changes in pressure in each reactor vessel headspace—the volume within each vessel that separates the liquid reagents from the vessel's sealed cap. During reaction, any changes in the head space pressure, at constant temperature, reflect changes in the amount of gas present in the head space. Reactor system 100 uses this pressure data to determine the molar production or consumption rate $r_i$ of a gaseous component since, for an ideal gas at constant temperature, $$r_i = \frac{1}{RT}\frac{dp_i}{dt} \qquad \text{(Eq. 11)}$$

where R is the universal gas constant and $p_i$ is the partial pressure of the ith gaseous component. Reactor control system 100 receives data from temperature sensors 232 that can be used to account for changes in pressure resulting from variations in head space temperature. The ideal gas law or similar equation of state can be used to calculate the pressure correction.

Alternatively, valves 245 are used to compensate for the consumption of a gaseous reactant in a reaction where there is a net loss in moles of gas-phase components. At the beginning of the reaction, valves 245 open to allow gas to enter each of the vessels 210. Once the pressure within each of the vessels, as read by the sensor 242, reaches a predetermined value $P_H$, pressure controller 243 causes valves 245 to close. As the reaction consumes the source gas, the total pressure within each of the vessels 210 decreases. Once the pressure in a particular vessel falls below a predetermined value $P_L$, reactor control system 100, through pressure controller 243, opens the valve 245 associated with the particular vessel, repressurizing it to $P_H$ This process—filling each of the vessels with source gas to $P_H$, allowing the head space pressure to drop below $P_L$, and then refilling the vessels with source gas to $P_H$—is usually repeated many times during the course of the reaction. Furthermore, the total pressure in the head space of each of the vessels 210 is continuously monitored and recorded during the gas fill-pressure decay cycle.

An analogous method can be used to investigate reactions where there is a net gain of gas-phase components. At the beginning of a reaction, all reaction materials are introduced into the vessels 210 and the valves 245 are closed. As the reaction proceeds, gas production results in a rise in head space pressure, which sensors 242 and reactor control system 100 monitor and record. Once the pressure within a particular vessel reaches $P_H$, reactor control system 100 directs the controller 243 to open the appropriate valve 245 to depressurize the vessel. Once the head space pressure falls below $P_L$, reactor control system 100 instructs the controller 243 to close the valve 245. The total pressure is continuously monitored and recorded during the gas rise-vent cycle.

Reactor control system 100 can estimate gas consumption (production) rates from the total pressure data by a variety of methods. One estimate of gas consumption (production) can be made from the slope of the pressure decay (growth) curves obtained when the valve is closed. These data, after converting total pressure to partial pressure based on reaction stoichiometry, can be inserted into Equation 6 to calculate $r_i$, the molar consumption (production) rate. A second estimate can be made by assuming that a fixed quantity of gas enters (exits) the vessel during each valve cycle. The frequency at which the reactor is repressurized (depressurized) is therefore proportional to the gas consumption (production) rate. A third, more accurate estimate can be obtained by assuming a known gas flow rate through the valve. Multiplying this value by the time during which the valve remains open yields an estimate for the quantity of gas that enters or leaves the vessel during a particular cycle. Dividing this product by the time between the next valve cycle—that is, the time it takes for the pressure in the vessel head space to fall from $P_H$ to $P_L$—yields an average value for the volumetric gas consumption (production) rate for the particular valve cycle. Summing the quantity of gas added during all of the cycles equals the total volume of gas consumed (produced) during the reaction.

Operation of a Reactor Control System

Figure 4:
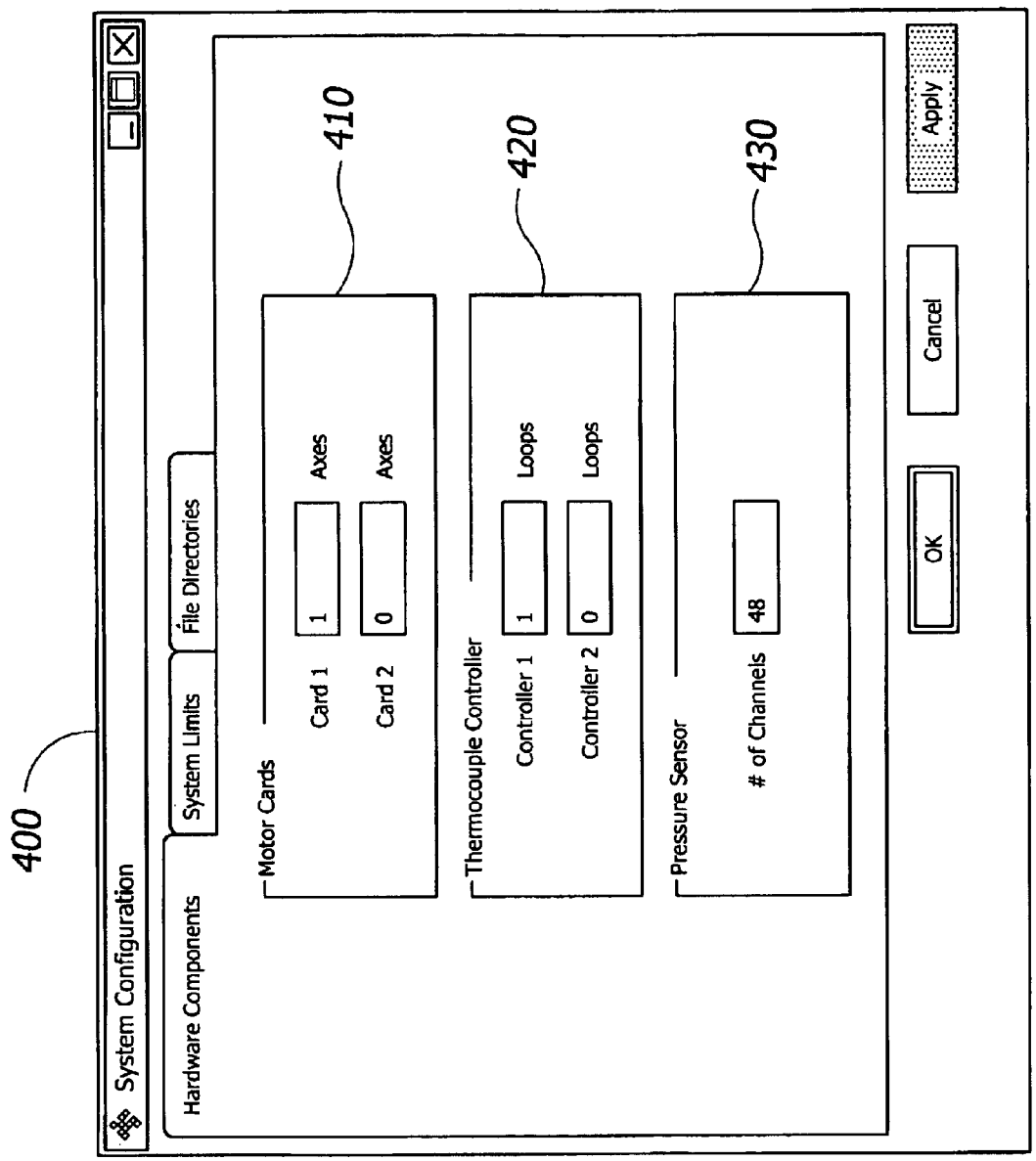
FIG. 4 is an illustration of a dialog window for user input of system configuration information.

Referring to FIG. 4, reactor control system 100 receives system configuration information from the user through system configuration window 400, displayed on monitor 150. System configuration window 400 allows the user to specify the appropriate hardware components for an experiment. For example, the user can choose the number of motor cards 224 and the set a number of motor axes per card in motor pane 410. Temperature controller pane 420 allows the user to select the number of separate temperature controllers 236 and the number of reactor vessels (the number of feedback control loops) per controller. In pressure sensor pane 430, the user can set the number of pressure channels corresponding to the number of reactor vessels in reactor 110. The user can also view the preset safety limits for motor speed, temperature and pressure through system configuration window 400.

Figure 5:
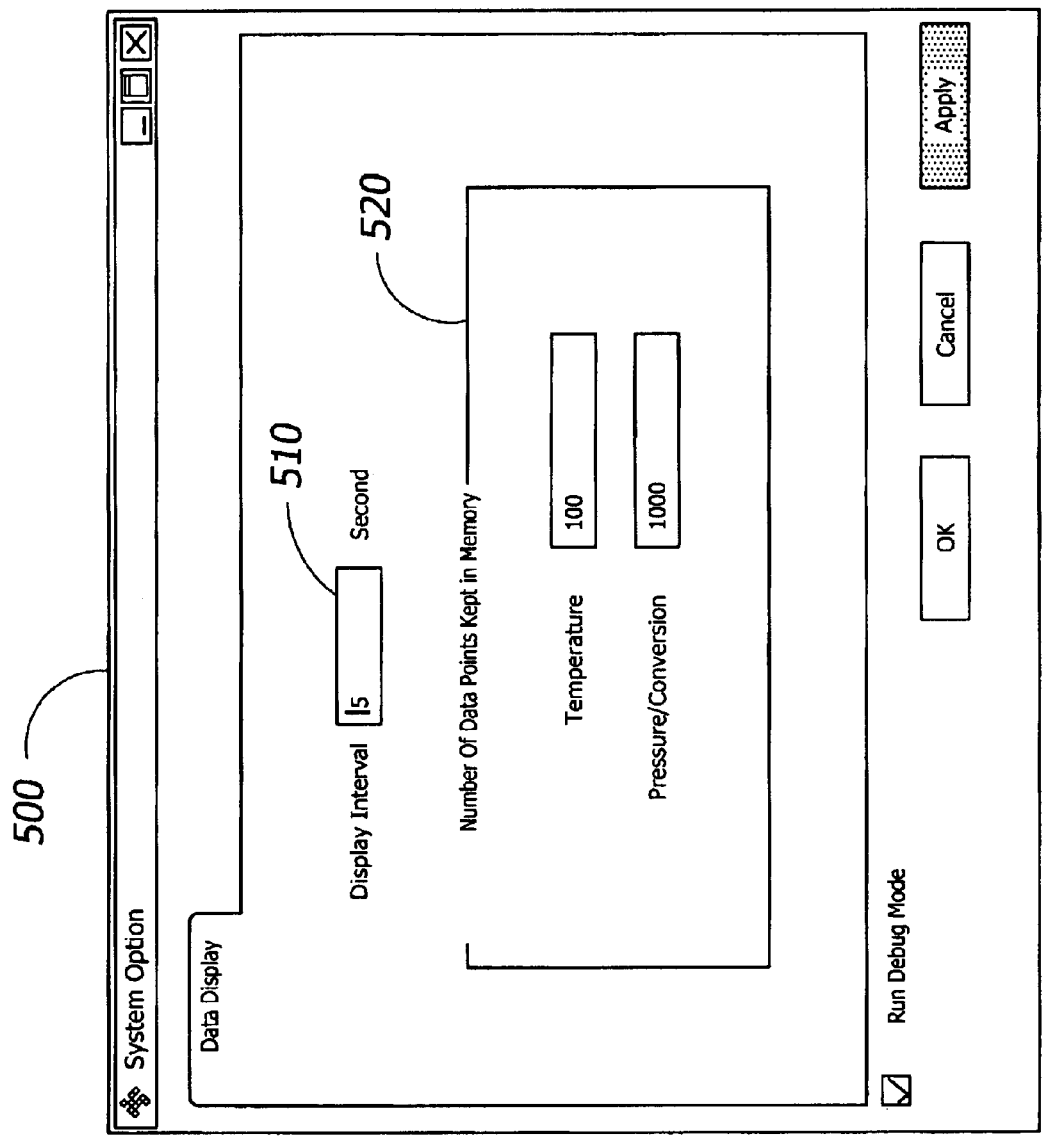
FIG. 5 is an illustration of a dialog window for user input of data display information.

As shown in FIG. 5, reactor control system 100 receives data display information from the user through system option window 500. Display interval dialog 510 lets the user set the refresh interval for data display. The user can set the number of temperature and pressure data points kept in memory in data point pane 520.

Figure 6A:
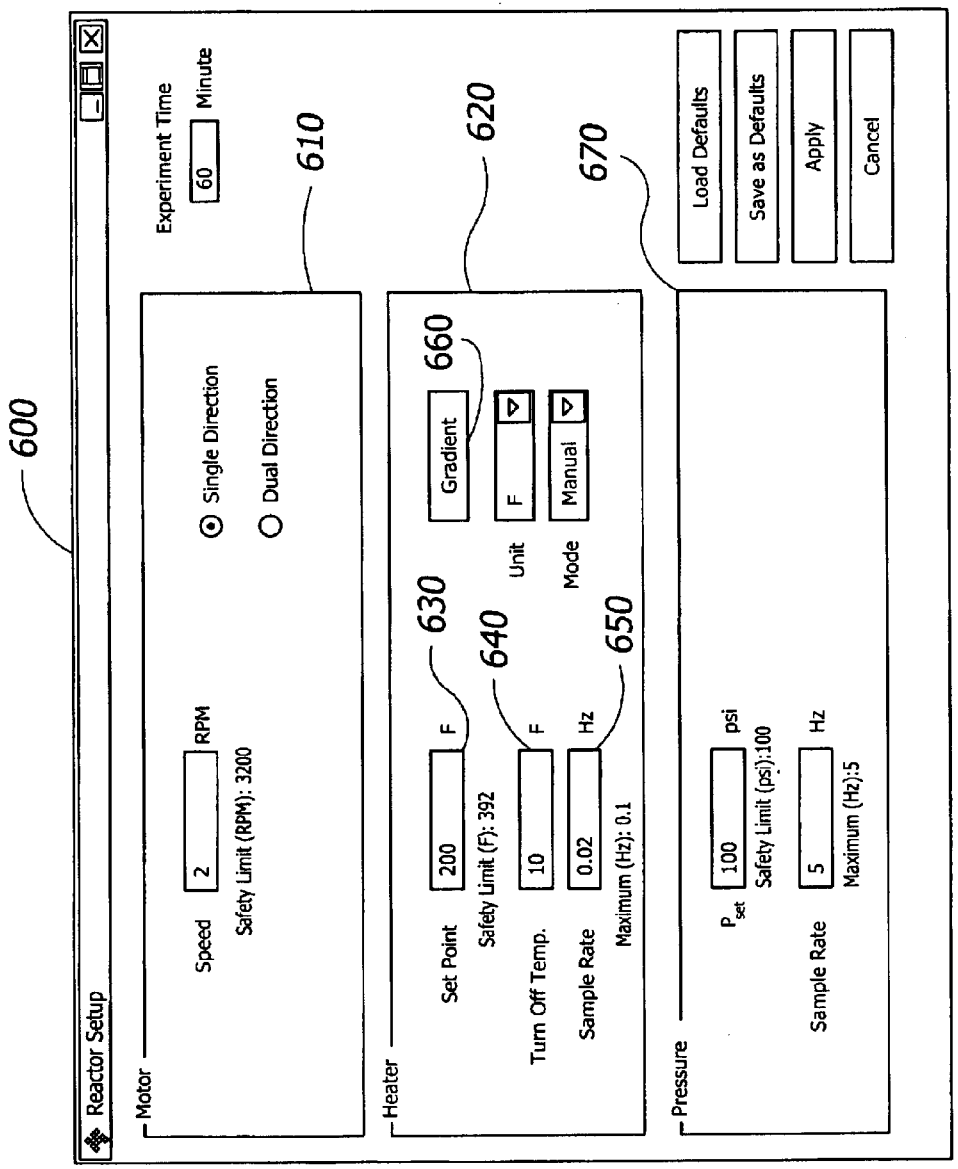
FIG. 6a is an illustration of a dialog window for user input of parallel reactor parameters.

At any time before or during an experiment, the user can enter or modify reaction parameters for each reactor vessel 210 in reactor block 200 using reactor setup window 600, shown in FIG. 6a. In motor setup pane 610, the user can set a motor speed (subject to any preset safety limits), and can also select single or dual direction motor operation. The user can specify temperature parameters in temperature setup pane 620. These parameters include temperature set point 630, turn off temperature 640, sampling rate 650, as well as the units for temperature measurement and temperature controller operation modes. By selecting gradient button 660, the user can also set a temperature gradient, as will be discussed below. Pressure parameters, including a pressure set point and sampling rate, can be set in pressure setup pane 670. Panes 610, 620 and 670 can also display safety limits for motor speed, temperature and pressure, respectively. The values illustrated in FIG. 6a are not intended to limit this invention and are illustrative only. Reactor setup window 600 also lets the user set a time for the duration of the experiment. Reactor setup window 600 lets the user save any settings as defaults for future use, and load previously saved settings.

Figure 6B:
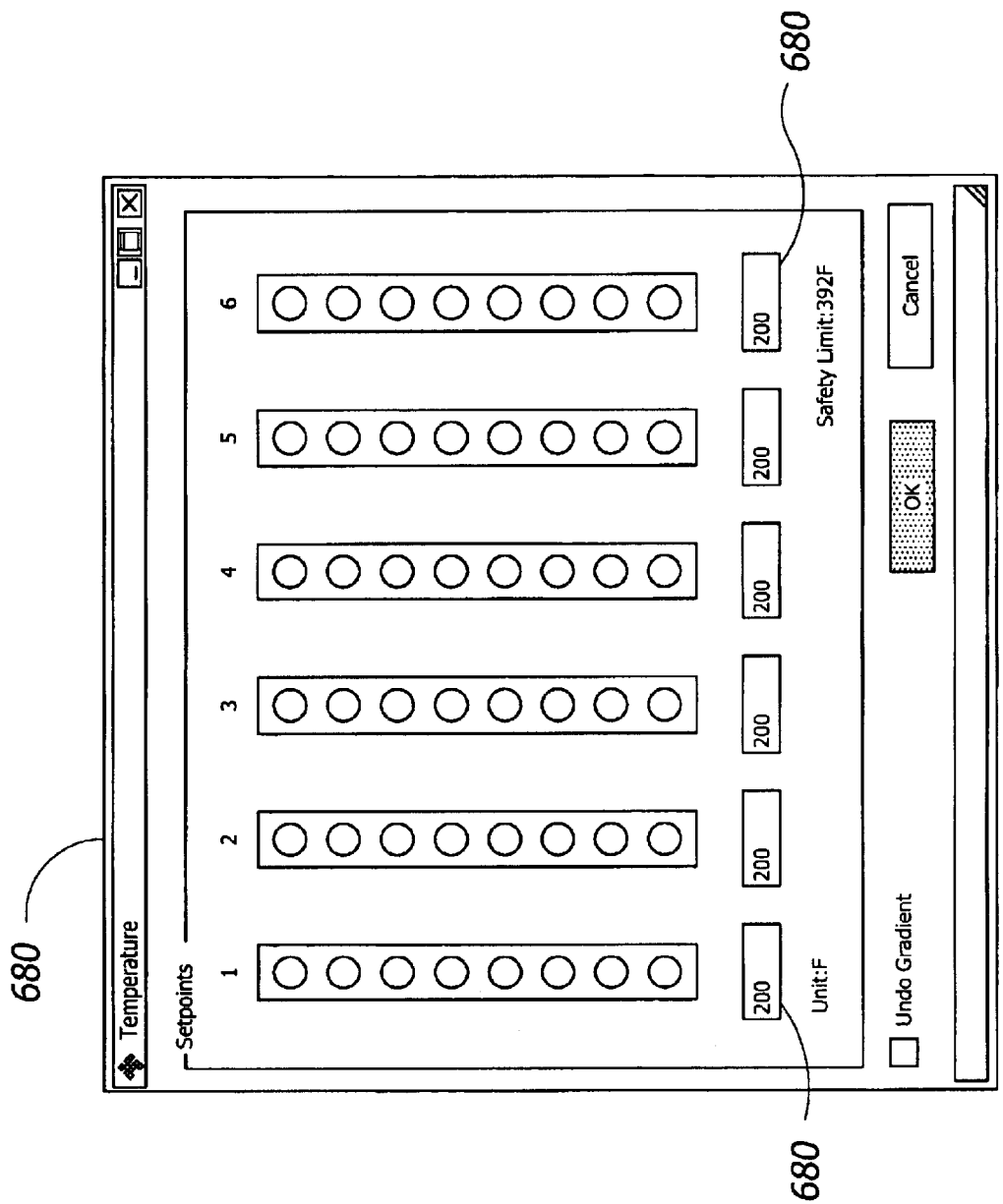
FIG. 6b is an illustration of a dialog window for user input of a temperature gradient for reactor blocks in a parallel reactor.

FIG. 6b illustrates the setting of a temperature gradient initiated by selecting gradient button 660. In gradient setup window 680, the user can set a temperature gradient across reactor 110 by entering different temperature set points 690 for each reactor block module of a multi-block reactor 110. As with other setup parameters, such temperature gradients can be saved in reactor setup window 600.

Figure 7A:
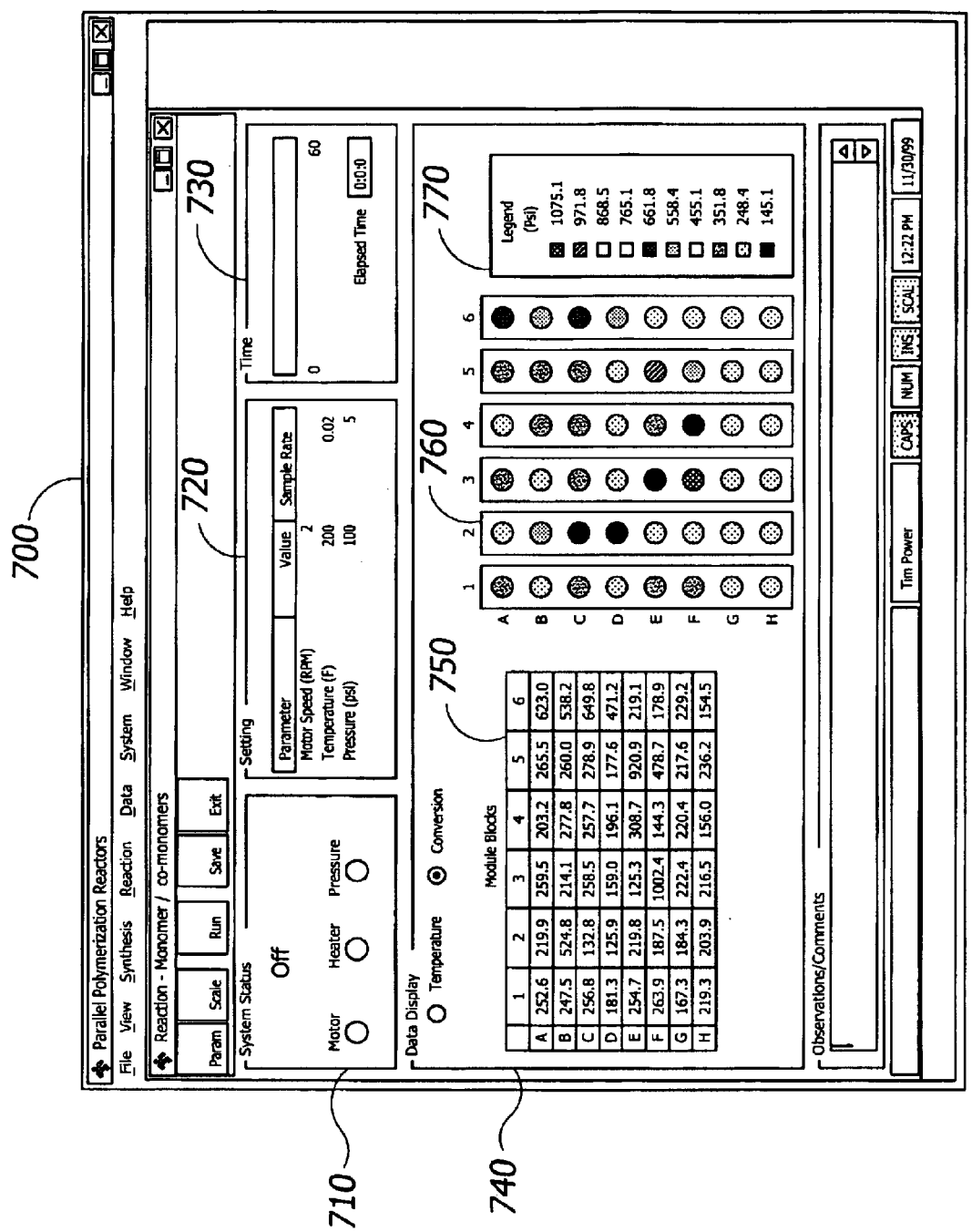
FIGS. 7a–7b are illustrations of windows displaying system status and experimental results for a parallel reactor.
Figure 7B:
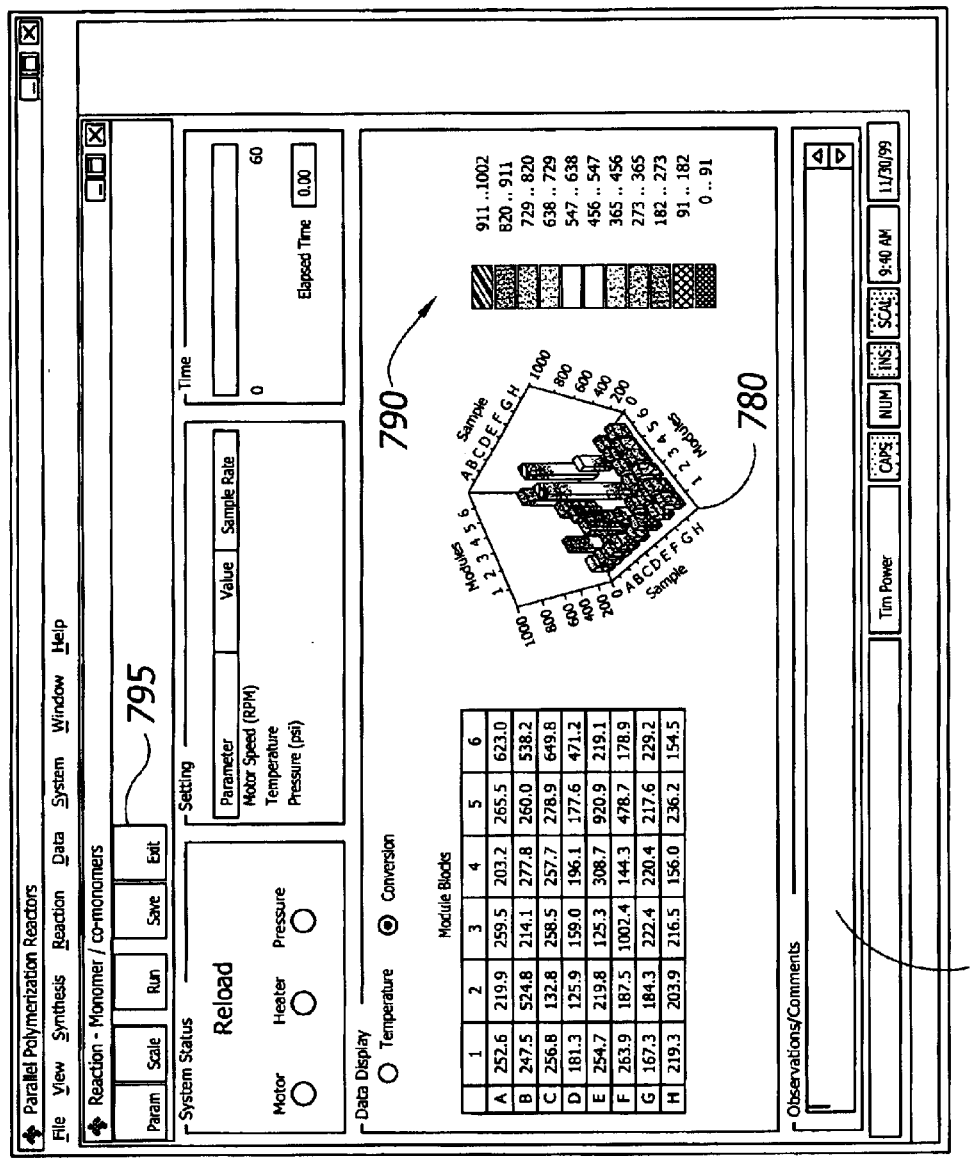

Referring to FIG. 7a, the user can monitor an experiment in reaction window 700. System status pane 710 displays the current system status, as well as the status of the hardware components selected in system configuration window 400. Setting pane 720 and time pane 730 display the current parameter settings and time selected in reactor setup window 600, as well as the elapsed time in the experiment. Experimental results are displayed in data display pane 740, which includes two dimensional array 750 for numerical display of data points corresponding to each reactor vessel 210 in reactor 110, and graphical display 760 for color display of the data points displayed in array 750. Color display 760 can take the form of a two dimensional array of reactor vessels or three dimensional color histogram 780, shown in FIG. 7b.

The color range for two dimensional array 760 and histogram 780 is displayed in legends 770 and 790, respectively. Data display pane 740 can display either temperature data or conversion data calculated from pressure measurements as described above. In either case, the displayed data is refreshed at the rate set in the system options window 500.

Figure 8:
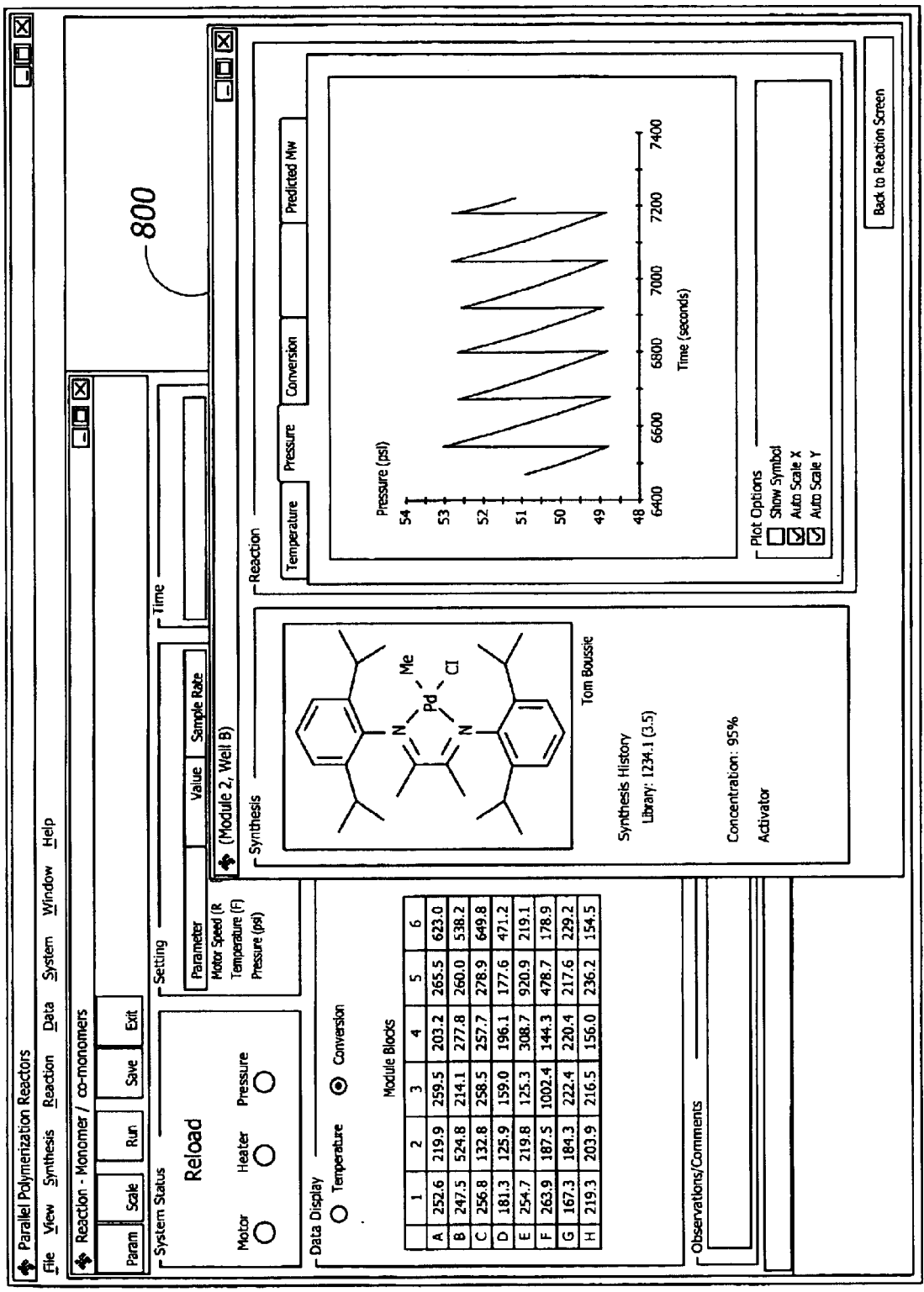
FIG. 8 is an illustration of a window displaying experimental results for a single reactor vessel.

By selecting an individual reactor vessel 210 in data display pane 740, the user can view a detailed data window 800 for that vessel, as shown in FIG. 8. Data window 800 provides a graphical display of experimental results, including, for example, temperature, pressure, conversion and molecular weight data for that vessel for the duration of the experiment.

Referring again to FIG. 7b, toolbar 795 lets the user set reactor parameters (by entering reactor setup window 600) and color scaling for color displays 760 and 780. The user can also begin or end an experiment, save results and exit system 100 using toolbar 795. The user can enter any observations or comments in comment box 798. User comments and observations can be saved with experimental results.

Figure 9:
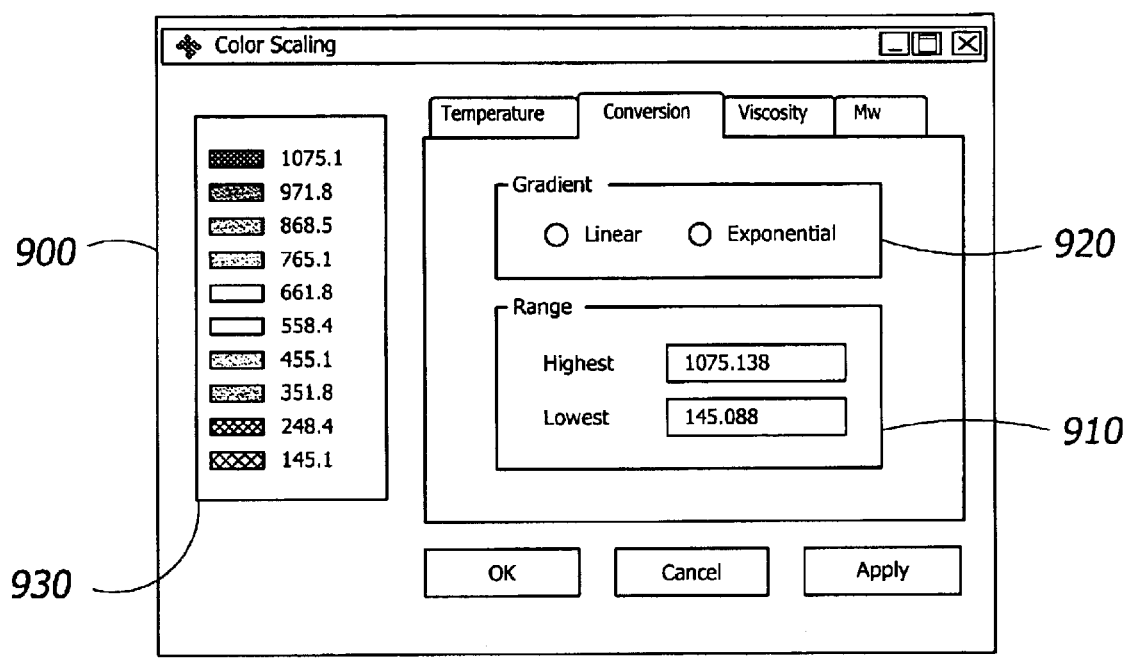
FIG. 9 is an illustration of a dialog window for user input of color scaling parameters.

Referring to FIG. 9, the user can set the color scaling for color displays 760 and 780 through color scaling window 900. Color scaling window 900 lets the user select a color range corresponding to temperature or conversion in color range pane 910. The user can also set a color gradient, either linear or exponential, through color gradient pane 920. Color scaling window 900 displays the selected scale in color legend 930.

The invention can be implemented in digital electronic circuitry, or in computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language.

Suitable computer programs in modules 140 and 145 can be implemented in classes as set forth in the following tables. (The prefix "o" in a name indicates that the corresponding property is a user-defined object; the prefix "c" in a name indicates that the corresponding property is a collection.)

1. Application Class

Property Table:

| Category | Name | Access | Description/Comments |
|---|---|---|---|
| General | ClsName | Get | Class name |
|  | AppName | Get | Application name |
|  | sRootDir | Get/Let | Root directory of all system files |
|  | bDebugMode | Get/Let | System running mode. If TRUE, display message boxes for errors in addition to error logging. If FALSE, log the error to the log file |
|  | DBIsConnected | Get/Let | Whether database is connected |
| System Registry | SectionGeneral | Get | General section |
|  | SectionSystemLimits | Get | Section for System Limit Values |
|  | SectionDefaultParam | Get | Section for system default parameters |
| ColorScaling | oTempScale | Get | Color Scale object for temperature data |
|  | oViscosityScale | Get | Color Scale object for viscosity data |
|  | oConversionScale | Get | Color Scale object for conversion data |
|  | oMWScale | Get | Color Scale object for molecule weight data |

Method Table:

| Name | Argument List | Return Type | Description/Comments |
|---|---|---|---|
| SaveCnfg |  | Boolean | Save application configurations to the system registry |

2. ColorScale Class

Parent Class: Application

Property Table:

| Name | Access | Description/Comments |
|---|---|---|
| ClsName | Get | Class name |
| Highest | Get/Let | Highest value |
| Lowest | Get/Let | Lowest value |
| GradientType | Get/Let | Type of the gradient between the lowest and highest to the log file |
| LegendValues | Get | A collection of legend values |

Method Table:

| Name | Argument List | Return Type | Description/Comments |
|---|---|---|---|
| SetLegendValues |  |  | Recalculate the legend values according to the current property values |
| GetLegendColor | fValue | long | Get color of the specified data value |

3. ColorLegend Class

Parent Class: ColorScale

Property Table:

| Name | Access | Description/Comments |
|---|---|---|
| ClsName | Get | Class Name |
| ColorCount | Get | Number of colors used in the legend |

Method Table:

| Name | Argument List | Return Type | Description/Comments |
|---|---|---|---|
| GetColorValue | fValue | long | Get color for the specified data value |

4. System Class

Property Table:

| Category | Name | Access | Description/Comments |
|---|---|---|---|
| General | ClsName | Get | |
| | ExpID | | |
| System Status | Status | Get/Let | Status variable |
| | STATUS_OFF | Get | constant |
| | STATUS_RUN | Get | constant |
| | STATUS_IDLE | Get | constant |
| | STATUS_ERROR | Get | constant |
| System Timing | oExpTiming | Get | Control and record the experiment time |
| | oDisplayTiming | Get | Control the data display updating rate |
| System Alarming | oAlarm | Get | Provide alarm when system error occurs |
| System Components | oMotors | Get | |
| | oHeaters | Get | |
| | oPressures | Get | |

Method Table:

| Name | Argument List | Return Type | Description/Comments |
|---|---|---|---|
| Run | | | |
| StopRunning | | | |
| Archive | | | |

5. ExpTiming Class

Parent Class: System

Property Table:

| Name | Access | Description/Comments |
|---|---|---|
| ClsName | Get | Class Name |
| TimingByTime | Get/Let | Boolean type |
| TimingByPressure | Get/Let | Boolean type |
| TimingByTemperature | Get/Let | Boolean type |
| TargetTime | Get/Let | System will stop if specified target value is achieved |
| TargetPressure | Get/Let | System will stop if specified target value is achieved |
| TargetTemperature | Get/Let | System will stop if specified target value if achieved |
| ExpDate | Get/Let | Date when experiment starts to run |
| ExpStartTime | Get/Let | Time when experiment starts to run |
| ExpEndTime | Get/Let | Time when experiment stop running |
| ExpElapsedTime | Get/Set | The time passed during the experiment |
| TimerInterval | Let | Timer used to update the elapsed time |

Method Table:

| Name | Argument List | Return Type | Description |
|---|---|---|---|
| LoadDefaultExpTiming | | boolean | |
| SaveDefaultExpTiming | | boolean | |

6. DisplayTiming Class

Parent Class: System

Property Table:

| Name | Access | Description/Comments |
|---|---|---|
| ClsName | Get | Class Name |
| DisplayTimer | Get/Set | Timer used to update the data |
| TimerIntercal | Get/Let | |

Method Table:

| Name | Argument List | Return Type | Description |
|---|---|---|---|
| SaveDefaultParam | | Boolean | |

7. Alarm Class

Parent Class: System

Property Table:

| Name | Access | Description/Comments |
|---|---|---|
| ClsName | Get | Class Name |
| BeepTimer | Set | Timer used to control beep |
| PauseTimer | Set | Timer used to pause the beep |
| BeepStatus | Get | A boolean value: FALSE if paused, otherwise TRUE |
| BeepPauseTime | Let | Time duration for beep to pause |

Method Table:

| Name | Argument List | Return Type | Description |
|---|---|---|---|
| TurnOnBeep | | | Start to beep |
| TurnOffBeep | | | Stop beeping |

8. Motors class
Parent Class: System

Property Table:

| Name | Access | Description/Comments |
|---|---|---|
| ClsName | Get | Class Name |
| SpeedLimit | Get/Let | Safety Limit |
| MotorIsOn | Get/Let | Status variable |
| Card1AxesCount | Get/Let | Axes count in card1 |
| Card2AcesCount | Get/Let | Axes count in card2 |
| oMotorCard1 | Get | Motor card object |
| oMotorCard2 | Get | Motor card object |
| oSpinTimer | Get/Set | Timer for dual spin |
| FoundDLL | Get | Motion DLL |
| ErrCode | Get | Error code |

Method Table:

| Category | Name | Argument List | Return Type | Description |
|---|---|---|---|---|
| To/From system Registry | LoadDefaultParam | | boolean | |
| | SaveDefaultParam | | boolean | |
| | SaveCardAxesCount | | boolean | |
| | SaveSystemLimit | | boolean | |
| Create/Delete Card Objects | CreateCard1 | iAxesCount | | |
| | CreateCard2 | iAxesCount | | |
| | DeleteCard1 | | | |
| | DeleteCard2 | | | |
| Motor Control | Init | | boolean | For all axes |
| | Spin | iAxis, dSpeed | boolean | |
| | run | | boolean | For all axes |
| | StopRunning | | boolean | For all axes |
| Archive | ArchiveParam | iFileNo | boolean | |

9. MotorAxis Class
Parent Class: Motors

Property Table:

| Name | Access | Description/Comments |
|---|---|---|
| ClsName | Get | Class Name |
| Parent | Set | Reference to the parent object |
| MotorID | Get/Let | Motor Axis ID |
| oCurParam | Get | Reference to current parameter setting |

Method Table:

| Name | Argument List | Return Type | Description |
|---|---|---|---|
| GetParamSetting | [index] | MotorParam | Return the last in the parameter collection |
| Run | | boolean | Add oCurParam to the Param collection, and run this motor axis |

10. MotorParam Class
Parent Class: Motors

Property Table:

| Name | Access | Description/Comments |
|---|---|---|
| clsName | Get | Class Name |
| Parent | Set | Reference to the parent object |
| MotionType | Get/Let | Dual or single direction spin |
| DeltaT | Get/Let | Time duration before changing spin direction |
| SpinRate | Get/Let | Spin rate in RPM |
| EffectiveTime | Get/Let | Time the parameters take effect |

Method Table:

| Name | Argument List | Return Type | Description |
|---|---|---|---|
| PrintParam | iFileNo | Boolean | Print the parameters to file |

11. Heaters class
Parent Class: System

Property Table:

| Name | Access | Description/Comments |
|---|---|---|
| ClsName | Get | Class Name |
| oParent | Get | Reference to the parent object |
| TempLimit | Get/Let | Temperature Safety Limit |
| SplRateLimit | Get/Let | Sample Rate Limit |
| CtlrLoopCount | Get/Let | Loop count in controller1 |
| CtlrLoopCount | Get/Let | Loop count in controller2 |
| HeaterIsOn | Get/Let | Status variable |
| oHeaterCtlr1 | Get | Heater controller object as clsHeaterCtlr |
| oHeaterCtlr2 | Get | Heater controller object as clsHeaterCtlr |
| oData | Get | Data object as clsHeaterData |
| 1DataPointsInMem | Get/Let | Number of data points kept in memory |
| FoundDLL | Get | RS232 DLL. If found, 1, otherwise-1 |
| ErrCode | Get | Error Code |

Method Table:

| Category | Name | Argument List | Return Type | Descriptions |
|---|---|---|---|---|
| To/From system Registry | LoadDefaultParam | | boolean | |
| | SaveDefaultParam | | boolean | |
| | SaveCtlrLoopCount | | boolean | |
| | SaveSystemLimit | | boolean | |

-continued

Method Table:

| Category | Name | Argument List | Return Type | Descriptions |
|---|---|---|---|---|
| Create/Delete Ctlr Objects | Create Ctlr 1 | iLoopCount | | |
| | Create Ctlr 2 | iLoopCount | | |
| | Delete Ctlr 1 | | | |
| | Delete Ctlr 2 | | | |
| Heater Control | Init | | boolean | Open COM1, COM2 |
| | OutputHeat | | boolean | For all loops |
| | TurnOff | | boolean | For all loops |
| | GetTemp | | boolean | For all loops |
| | SafetyMonitor | Icount,vData | | Check Temperature |
| | SafetyHandler | | | |
| Archive | ArchiveParam | iFileNo | boolean | |

12. HeaterCtlr class

Parent Class: Heaters

Property Table:

| Name | Access | Description/Comments |
|---|---|---|
| ClsName | Get | Class Name |
| Parent | Set | Reference to the parent object |
| oCurParam | Get | Reference to current parameter setting |

Method Table:

| Name | Argument List | Return Type | Description |
|---|---|---|---|
| AddParamSetting | oParam | boolean | Add the parameter object to the parameter collection |
| GetParamSetting | [index] | HeaterParam | Return the last in the parameter collection |

13. HeaterParam Class

Parent Class: HeaterCtlr

Property Table:

| Name | Access | Description/Comments |
|---|---|---|
| clsName | Get | Class Name |
| Parent | Set | Reference to the parent object |
| Setpoint | Get/Let | Setpoint for temperature |
| SplRate | Get/Let | Sampling Rate (Hz) |
| EffectiveTime | Get/Let | Time the parameters take effect |

Method Table:

| Name | Argument List | Return Type | Description |
|---|---|---|---|
| PrintParam | iFileNo | Boolean | Print the parameters to file |

14. HeaterData Class

Parent Class: Heaters

Property Table:

| Name | Access | Description/Comments |
|---|---|---|
| clsName | Get | Class Name |
| Parent | Set | Reference to the parent object |
| DataPointsInMem | Let | |
| LoopCount | Let | Total loop count |
| DataCount | Get | Data point count |
| cTime | Get | Get time data collection |
| cTemp | Get | Get temperature data collection |

Method Table:

| Name | Argument List | Return Type | Description |
|---|---|---|---|
| GetData | ByRef fTime, ByRef vTemp [,index] | Boolean | Get current data set, or the data set with specified index |
| AddData | fTime, vTemp | | Add the data set to the data collections |
| ClearData | | | Clear the data collection |
| WriteToDisk | | | Write the current data to disk file |

15. Pressures Class

Parent Class: System

Property Table:

| Name | Access | Description/Comments |
|---|---|---|
| ClsName | Get | Class Name |
| oParent | Get | Reference to the parent object |
| PressureLimit | Get/Let | Pressure Safety Limit |
| SplRateLimit | Get/Let | Sample Rate Limit |
| ChannelCount | Get/Let | Analog Input channel count |
| PressureIsOn | Get/Let | Status variable |
| oData | Get | Data object as clsPressureData |
| lDataPointsInMem | Get/Let | Number of data points kept in memory |
| oCWAOP | Get | Object of analog output ActiveX control |
| oCWAIP | Get | Object of analog input ActiveX control |
| ErrCode | Get | Error code |

Method Table:

| Category | Name | Argument List | Return Type | Description |
|---|---|---|---|---|
| To/From System Registry | LoadDefaultParam | | boolean | |
| | SaveDefaultParam | | boolean | |
| | SaveChannelCount | | boolean | |
| | SaveDataPointsInMem | | | |
| | SaveSystemLimit | | boolean | |
| Pressure System Control | Analog Output | | boolean | Output Pset |
| | GetAIData | | boolean | Analog Input |
| Archive | ArchiveParam | iFileNo | boolean | |

16. PressureParam Class

Parent Class: Pressures

Property Table:

| Name | Access | Description/Comments |
|---|---|---|
| clsName | Get | Class Name |
| Parent | Set | Reference to the parent object |
| Setpoint | Get/Let | Setpoint for pressure (psi) |
| SplRate | Get/Let | Sampling Rate (Hz) |
| EffectiveTime | Get/Let | Time the parameters take effect |

Method Table:

| Name | Argument List | Return Type | Description |
|---|---|---|---|
| PrintParam | iFileNo | Boolean | Print the parameters to the file |

17. PressureData Class

Parent Class: Pressures

Property Table:

| Name | Argument | Access | Description/Comments |
|---|---|---|---|
| clsName | | Get | Class Name |
| Parent | | Set | Reference to the parent object |
| DataPointsInMem | | Let | |
| ChannelCount | | Let | Total AI channel count |
| PresCount | | Get | Pressure data point count |
| ConvCount | | Get | Conversion data point count |
| cPresTime | | Get | Get time collection for pressure data |
| cPressure | | Get | Get pressure data collection |
| cConvTime | iChannelNo | Get | Get time collection for conversion data |
| cConversion | iChannelNo | Get | Get conversion data collection |

Method Table:

| Name | Argument List | Return Type | Description |
|---|---|---|---|
| GetCurPres | ByRef vPres | Boolean | Get current pressure data set |
| GetCurConv | ByRef vConv | Boolean | Get current conversion data set |
| AddPres | fTime, vPres | | Add the pressure data set to the pressure data collections, then calculate conversions |
| ClearData | | | Clear all the data collections |
| WritePresToDisk | | Boolean | Write the current pressure data to disk file |
| WriteConvToDisk | | Boolean | Write the current conversion data to disk file |

18. ErrorHandler Class
Property Table:

Property Table:

| Name | Access | Description/Comments |
|---|---|---|
| ClsName | Get | Class Name |
| LogFile | Get/Let | Log file for error messages |

Method Table:

| Name | Argument List | Return Type | Description |
|---|---|---|---|
| SaveConfg | | boolean | |
| OpenLogFile | iFileNo | boolean | Open log file with specified file number for APPEND, lock WRITE |
| OpenLogfile | iFileNo | boolean | Open log file with specified file number for APPEND, lock WRITE |
| CloseLogFile | | | |
| LogError | sModName, sFuncName, iErrNo, sErrText | | Write error messages to the log file, also call DisplayError in debug mode |
| DisplayError | sModName, sFuncName, iErrNo, sErrText | | Show messageBox to display the error |

Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented on a computer system having a display device such as a monitor or LCD screen for displaying information to the user and a keyboard and a pointing device such as a mouse or a trackball by which the user can provide input to the computer system. The computer system can be programmed to provide a graphical user interface through which computer programs interact with users.

Figure 10:
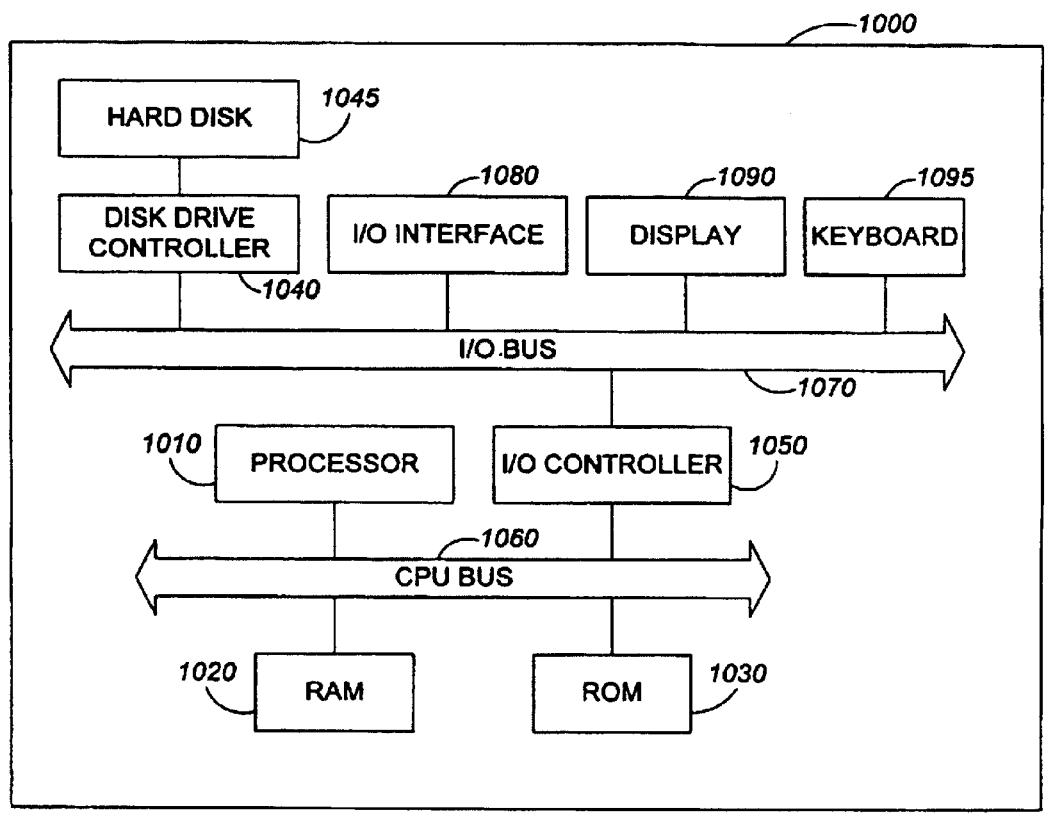
FIG. 10 is a schematic diagram of a computer platform suitable for implementing the data processing system of the invention.

An example of one such type of computer is shown in FIG. 10, which shows a block diagram of a programmable processing system 1000 suitable for implementing or performing the apparatus or methods of the invention. The system 1000 includes a processor 1010, a random access memory (RAM) 1020, a program memory 1030 (for example, a writable read-only memory (ROM) such as a flash ROM), a hard drive controller 1040, and an input/output (I/O) controller 1050 coupled by a processor (CPU) bus 1060. The system 1000 can be preprogrammed, in ROM, for example, or it can be programmed (and reprogrammed) by loading a program from another source (for example, from a floppy disk, a CD-ROM, or another computer).

The hard drive controller 1040 is coupled to a hard disk 1045 suitable for storing executable computer programs, including programs embodying the present invention, and data including the images, masks, reduced data values and calculated results used in and generated by the invention. The I/O controller 1050 is coupled by means of an I/O bus 1070 to an I/O interface 1080. The I/O interface 1080 receives and transmits data in analog or digital form over communication links such as a serial link, local area network, wireless link, and parallel link. Also coupled to the I/O bus 1070 is a display 1090 and a keyboard 1095. Alternatively, separate connections (separate buses) can be used for the I/O interface 1070, display 1090 and keyboard 1095.

The invention has been described in terms of particular embodiments. Other embodiments are within the scope of the following claims. Although elements of the invention are described in terms of a software implementation, the invention may be implemented in software or hardware or firmware, or any combination of the three. In addition, the steps of the invention can be performed in a different order and still achieve desirable results.

What is claimed is:

1. A method for monitoring a combinatorial chemistry experiment during which a plurality of reactions are simultaneously occurring substantially independent of each other in a plurality of reactor vessels, respectively, each of the plurality of vessels having one or more sensors associated therewith providing measured values relating to the reaction in the reactor vessels, said method comprising:
   (a) receiving the measured value associated with each of the plurality of reactor vessels;
   (b) storing the measured values in a memory;
   (c) repeating steps (a) and (b) multiple times during the course of the combinatorial chemical reactions;
   (d) processing experimental data comprising at least one of the stored measured values or comprising an experimental value calculated from at least one of the measured values; and
   (e) screening at least one of the reactions or at least one of the materials used in the reactions with respect to said experimental data of another of the reactions.

2. The method of claim 1, wherein said screening occurs during the course of the combinatorial chemical reactions.

3. The method of claim 1 wherein said screening comprises ranking said at least one of the reactions or at least one of the materials used in the reactions with respect to said experimental data of another of the reactions.

4. The method of claim 1, wherein processing experimental data comprises calculating process variables from the stored measured values and/or calculating product variables from the stored measured values.

5. The method of claim 1 wherein processing experimental data comprises processing the stored measured values.

6. The method of claim 1 wherein the experimental data comprises at least one selected from the following group: temperature, pressure, torque, power, mixing variables, stirring rate, motor speed, viscosity, reaction kinetics, reaction conversion, polymer concentration, polymer conversion, monomer conversion, percent conversion, molecular conversion, rate of conversion, rate of reaction, molecular weight, particle size, stability and catalyst related parameters.

7. The method of claim 6 wherein the experimental data comprises viscosity measurements to screen or characterize dilute suspensions of insoluble particles.

8. The method of claim 1, wherein receiving the measured value comprises receiving a set of values corresponding to reaction conditions associated with the plurality of reactor vessels.

9. The method of claim 1, wherein parameters of the vessels are controlled in response to control parameters and further comprising:
   changing at least one of the control parameters associated with the plurality of reactor vessels in response to the measured values.

10. The method of claim 9, wherein the changing step maintains the reactor vessel at a predetermined set point, and wherein the control parameters comprise at least one parameter selected from the following group: temperature, pressure, viscosity and motor speed.

11. The method of claim 1 further comprising displaying in graphical form the experimental data.

12. The method of claim 1, wherein step (c) is performed at a predetermined sampling rate.

13. The method of claim 1, further comprising:
   quenching a catalyst in at least one of the plurality of reactor vessels in response to the experimental data associated with the contents of the reactor vessel.

14. The method of claim 1, further comprising:
   using the experimental data to calculate an experimental value for at least one of the plurality of reactor vessels.

15. The method of claim 14, wherein the experimental value comprises at least one value selected from the following group: temperature change, pressure change, percent conversion of starting material and viscosity.

16. The method of claim 14, further comprising displaying the experimental value.

17. A computer program on a computer-readable medium for monitoring a combinatorial chemistry experiment during which a plurality of reactions are simultaneously occurring substantially independent of each other in a plurality of reactor vessels, respectively, each of the plurality of vessels having one or more sensors associated therewith providing measured values relating to the reaction in the reactor vessels, the program comprising instructions to:
   (a) receive a measured value associated with each of a plurality of reactor vessels;
   (b) store the measured values in a memory;
   (c) repeat steps (a) and (b) multiple times during the course of the combinatorial chemical reactions;
   (d) process experimental data comprising at least one of the stored measured values or comprising an experimental value calculated from at least one of the stored measured values; and (e) screen at least one of the reactions or at least one of the materials used in the reactions with respect to said experimental data of another of the reactions.

18. The computer program of claim 17, wherein the instructions to screen execute screening during the course of the combinatorial chemical reactions.

19. The computer program of claim 17, wherein the instructions to screen comprise instructions to rank said at least one of the reactions or at least one of the materials used in the reactions with respect to said experimental data of another of the reactions.

20. The computer program of claim 17, wherein the instructions to process experimental data comprise instructions to calculate process variables from the stored measured values and/or to calculate product variables from the stored measured values.

21. The computer program of claim 17 wherein the experimental data comprises at least one selected from the following group: temperature, pressure, torque, power, mixing variables, stirring rate, motor speed, viscosity, reaction kinetics, reaction conversion, polymer concentration, polymer conversion, monomer conversion, percent conversion, molecular conversion, rate of conversion, rate of reaction, molecular weight, particle size, stability and catalyst related parameters.

22. The computer program of claim 17 wherein the experimental data comprises viscosity measurements to screen or characterize dilute suspensions of insoluble particles.

23. The computer program of claim 17 further comprising instructions to store in a memory experimental values calculated from the measured values.

24. The computer program of claim 17 further comprising instructions to display the measured values or experimental values calculated from the measured values on a user interface module.

25. A system which monitors a combinatorial chemistry experiment during which a plurality of reactions are simultaneously occurring substantially independent of each other in a plurality of reactor vessels, respectively, each of the plurality of vessels having one or more sensors associated therewith providing measured values relating to the reaction in the reactor vessels, said system comprising:

(a) a receiver for receiving the measured value associated with the contents of each of the plurality of reactor vessels during the course of the combinatorial chemical reaction;

(b) a graphical display for simultaneously displaying during the course of the combinatorial chemical reaction the received measured values or experimental values calculated from the measured values; and (c) a data analysis module for processing experimental data comprising at least one of the measured values or comprising an experimental value calculated from at least one of the measured values for use in screening at least one of the reactions or at least one of the materials used in the reactions with respect to said experimental data of another of the reactions.

26. The system of claim 25, wherein the data analysis module screens during the course of the combinatorial chemical reactions.

27. The system of claim 25, wherein said screening by the data analysis module comprises ranking said at least one of the reactions or at least one of the materials used in the reactions with respect to said experimental data of another of the reactions.

28. The system of claim 25, wherein the data analysis module calculates process variables from the stored measured values and/or calculates product variables from the stored measured values.

29. The system of claim 25 wherein the experimental data comprises at least one selected from the following group: temperature, pressure, torque, power, mixing variables, stirring rate, motor speed, viscosity, reaction kinetics, reaction conversion, polymer concentration, polymer conversion, monomer conversion, percent conversion, molecular conversion, rate of conversion, rate of reaction, molecular weight, particle size, stability and catalyst related parameters.

30. The system of claim 25 wherein the experimental data comprises viscosity measurements to screen or characterize dilute suspensions of insoluble particles.

31. The system of claim 25 further comprising a control controlling parameters of the reactor vessels and changing the parameters in response to the received measured values received by the receiver.

32. The system of claim 25 wherein the display displays a tabular representation of the received measured values, and wherein the tabular array and the graphical representation are simultaneously displayed.

33. A system which monitors a combinatorial chemistry experiment during which a plurality of reactions are simultaneously occurring substantially independent of each other in a plurality of reactor vessels, respectively, each of the plurality of vessels having one or more sensors associated therewith providing measured values relating to the reaction in the reactor vessels, said system comprising:

(a) a receiver for receiving the measured value associated with the contents of each of the plurality of reactor vessels during the course of the combinatorial chemical reaction;

(b) a storage media for storing during the course of the combinatorial chemical reaction the received measured values or experimental values calculated from the measured values; and (c) a data analysis module for processing experimental data comprising at least one of the stored measured values or comprising an experimental value calculated from at least one of the measured values for use in screening at least one of the reactions or at least one of the materials used in the reactions with respect to said experimental data of another of the reactions.

34. The system of claim 33, wherein the data analysis module screens during the course of the combinatorial chemical reactions.

35. The system of claim 33, wherein said screening by the data analysis module comprises ranking said at least one of the reactions or at least one of the materials used in the reactions with respect to said experimental data of another of the reactions.

36. The system of claim 33, wherein the data analysis module calculates process variables from the stored measured values and/or calculates product variables from the stored measured values.

37. The system of claim 33 wherein the experimental data comprises at least one selected from the following group: temperature, pressure, torque, power, mixing variables, stirring rate, motor speed, viscosity, reaction kinetics, reaction conversion, polymer concentration, polymer conversion, monomer conversion, percent conversion, molecular conversion, rate of conversion, rate of reaction, molecular weight particle size, stability and catalyst related parameters.

38. The system of claim 33 wherein the experimental data comprises viscosity measurements to screen or characterize dilute suspensions of insoluble particles.

39. The system of claim 33 further comprising a control controlling parameters of the reactor vessels and changing the parameters in response to the received measured values received by the receiver.

40. The system of claim 33 wherein the display displays a tabular representation of the received measured values, and wherein the tabular array and the graphical representation are simultaneously displayed.

41. A method of monitoring a combinatorial chemistry experiment during which a plurality of reactions are simultaneously occurring substantially independent of each other in a plurality of reactor vessels, respectively, each of the plurality of vessels having one or more sensors associated therewith providing measured values relating to the reaction in the reactor vessels, said method comprising:
  (a) receiving the measured value associated with each of the plurality of reactor vessels during the course of the combinatorial chemical reaction;
  (b) displaying or storing the received measured values or experimental values calculated from the measured values, and
  (c) screening the reactions or materials used in the reactions by processing experimental data comprising the measured values or experimental values calculated from the measured values for use in screening at least one of the reactions or at least one of the materials used in the reactions with respect to said experimental data of another of the reactions.

42. The method of claim 41 wherein said screening occurs during the course of the combinatorial chemical reactions.

43. The method of claim 41 wherein said screening comprises ranking said at least one of the reactions or at least one of the materials used in the reactions with respect to said experimental data of another of the reactions.

44. The method of claim 41, wherein processing experimental data comprises calculating process variables from the stored measured values and/or calculating product variables from the stored measured values.

45. The method of claim 41, wherein the experimental data comprises at least one selected from the following group: temperature, pressure, torque, power, mixing variables, stirring rate, motor speed, viscosity, reaction kinetics, reaction conversion, polymer concentration, polymer conversion, monomer conversion, percent conversion, molecular conversion, rate of conversion, rate of reaction, molecular weight, particle size, stability and catalyst related parameters.

46. The method of claim 41 wherein the experimental data comprises viscosity measurements to screen or characterize dilute suspensions of insoluble particles.

* * * * *

UNITED STATES PATENT AND TRADEMARK OFFICE
CERTIFICATE OF CORRECTION

PATENT NO. : 6,727,096 B1
DATED : April 27, 2004
INVENTOR(S) : Wang et al.

It is certified that error appears in the above-identified patent and that said Letters Patent is hereby corrected as shown below:

Column 26,
Line 64, delete "weight" and insert -- weight, --

Signed and Sealed this

Eighth Day of March, 2005

JON W. DUDAS
*Director of the United States Patent and Trademark Office*